(12) United States Patent
Anderson

(10) Patent No.: US 7,704,501 B2
(45) Date of Patent: Apr. 27, 2010

(54) ANTIBODIES BINDING TO HUMAN ATAXIN-1-LIKE POLYPEPTIDE

(75) Inventor: Dirk M. Anderson, Port Townsend, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 11/592,413

(22) Filed: Nov. 2, 2006

(65) Prior Publication Data

US 2007/0048310 A1  Mar. 1, 2007

Related U.S. Application Data

(62) Division of application No. 10/997,561, filed on Nov. 23, 2004, now Pat. No. 7,183,380, which is a division of application No. 10/207,706, filed on Jul. 26, 2002, now Pat. No. 6,887,687.

(60) Provisional application No. 60/309,056, filed on Jul. 30, 2001.

(51) Int. Cl.
*A61K 39/395* (2006.01)
*A61K 39/00* (2006.01)
*C12P 21/08* (2006.01)

(52) U.S. Cl. ............ 424/141.1; 424/142.1; 424/135.1; 424/130.1; 435/70.21

(58) Field of Classification Search ............... None
See application file for complete search history.

(56) References Cited

U.S. PATENT DOCUMENTS 5,834,183 A   11/1998   Orr et al.
6,280,938 B1   8/2001   Ranum et al.

FOREIGN PATENT DOCUMENTS

WO   WO 99/36527 A1   7/1999
WO   WO 01/75067 A2   11/2001

OTHER PUBLICATIONS

Burgess et al. J of Cell Bio. 1990. 111:2129-2138.*
Pawson et al. 2003, Science 300:445-452.*

* cited by examiner

*Primary Examiner*—Christine J Saoud
*Assistant Examiner*—Chang-Yu Wang
(74) *Attorney, Agent, or Firm*—Christine M. Bellas

(57) ABSTRACT

This invention relates to IMX97018, a new members of the human ataxin-1-like polypeptide family, methods of making such polypeptides, and to methods of using them to diagnose and treat neurological conditions and to identify compounds that alter IMX97018 polypeptide activities.

3 Claims, No Drawings

ANTIBODIES BINDING TO HUMAN ATAXIN-1-LIKE POLYPEPTIDE

CROSS-REFERENCE TO RELATED APPLICATIONS

This application is a divisional of U.S. application Serial No. 10/997,561, filed Nov. 23, 2004, now U.S. Pat. No. 7,183,380, which is a divisional of U.S. application Ser. No. 10/207,706, filed Jul. 26, 2002, now U.S. Pat. No. 6,887,687, which claims the benefit under 35 U.S.C. 119(e) of U.S provisional application Serial No. 60/309,056, filed Jul. 30, 2001. The entire disclosQres of these applications are relied upon and incorporated by reference herein.

FIELD OF THE INVENTION

This invention relates to IMX97018, a new ataxin-1-like human polypeptide, and to methods of making and using IMX97018 polypeptides.

BACKGROUND OF THE INVENTION

Ataxin-1 is one of a group of polypeptides implicated in spinocerebrellar ataxia (SCA) conditions, also called autosomal dominant cerebellar ataxias (ADCAs). SCA disorders are heritable autosomal dominant neurodegenerative conditions commonly featuring progressive ataxia, which is irregularity of muscle action due to failure of muscle coordination. Examples of other symptoms typically shown by patients diagnosed with SCA are paralysis of the ocular muscles (ophthalmoplegia) and loss of articulation of speech (dysarthria), as associated with SCA2 and SCA7; degeneration and loss of types of brain cells, as in loss of cerebellar Purkinje cells in SCA1 for example; and dementia, as associated with SCA2 and SCA6.

Several of the SCA disorders are characterized by genetic anticipation, which is the tendency of certain diseases to appear at earlier onset ages and/or with increased severity in each successive generation. In many cases, genetic anticipation has been shown to have a biological basis in the expansion in length of a stretch of triplet repeats that encode a particular amino acid. SCA1 shows genetic anticipation and is associated with expansions in the size of a polyglutamine tract in ataxin-1 polypeptide encoded by repeated CAG codons (Matilla et al., 1993, Presymptomatic analysis of spinocerebellar ataxia type 1 (SCA1) via the expansion of the SCA1 CAG-repeat in a large pedigree displaying anticipation and parental male bias, *Hum Molec Genet* 2: 2123-2128). Genetic anticipation has also been observed in families afflicted with several other of the SCA disorders such as SCA2, SCA3, SCA5, SCA6, SCA7, SCA8, SCA10, and in addition to the ataxin-1 gene of SCA1, expansions of CAG repeats have been found in alleles of those SCA genes that have been characterized to date: the SCA2/ataxin-2, SCA3/MJD1, SCA6/CACNA1A, and SCA7/ataxin-7 genes. Therefore, all of the SCA genes that have been studied at the molecular level indicate that expansions of CAG repeats are correlated with the genetic anticipation observed in the corresponding SCA disorder. While family history evidence has also been presented for genetic anticipation in SCA4 (Flanigan et al., 1996, *Am J Hum Genet* 59: 392-399), the SCA4 gene has not yet been identified and characterized.

Ataxin-1, -2, and -7, ataxin-3/MJD1, and CACNA1A polypeptides are detected in the cytoplasm of many types of neural cells, with the levels of expression varying from cell type to cell type, and with overlapping but non-identical patterns of expression displayed by these different polypeptides. The formation of nuclear inclusion bodies immunoreactive for these SCA-related polypeptides is positively correlated with the length of the polyglutamine tracts in the polypeptides. Interactions of these polypeptides with several different types of binding partners have been reported, and these interactions are believed to contribute in different ways to development of the SCA disease condition. For example, ataxin-1 polypeptide has been found to associate with cerebellar leucine-rich acidic nuclear protein (LANP) in the nuclear matrix of Purkinje cells, the primary site of the pathological effects of SCA1 (Matilla et al., 1997, *Nature* 389: 974-978). Association with nuclear proteins is thought to alter the conformation of ataxin-3/MJD1 polypeptide, exposing the polyglutamine tract (Perez et al., 1999, *Hum Mol Genet* 8: 2377-2385). Certain SCA-related polypeptides have been reported to have RNA-binding activity, either as part of the SCA-related polypeptide itself, or by binding to a polypeptide with RNA-binding activity. For example, ataxin-1 polypeptide binds RNA in vitro, with the RNA-binding capability inversely proportional to the length of the polyglutamine tract (Yue et al., 2001, *Hum Mol Genet* 10: 25-30), and ataxin-2 interacts with ataxin-2 binding protein 1 (A2BP1), a polypeptide containing RNA-binding motifs (Shibata et al., 2000, *Hum Mol Genet* 9: 1303-1313). Interestingly, in cells containing ataxin-1 with an expanded glutamine tract, down-regulation of particular neuronal genes is postulated to be an early step in SCA1 pathogenesis (Lin et al., 2000, *Nat Neurosci* 3: 157-163). In addition, there is evidence that polyglutamine tracts tend to self-associate, sequestering polypeptides containing them in nuclear inclusions and possibly trapping other polypeptides required for cell viability, such as CREB-binding protein (CBP) (McCampbell et al., 2000, *Hum Mol Genet* 9: 2197-2202). One possible outcome of expression of polyglutamine-containing polypeptides in neural cells is cell death through a non-apoptotic mechanism (Evert et al., 1999, *Hum Mol Genet* 8: 1169-1176).

In order to develop more effective treatments for spinocerebellar conditions and diseases, such as SCA1 and SCA4, information is needed about previously unidentified or uncharacterized SCA-related polypeptides.

SUMMARY OF THE INVENTION

The present invention is based upon the discovery of a new human ataxin-1-like polypeptide, IMX97018.

The invention provides an isolated polypeptide consisting of, consisting essentially of, or more preferably, comprising an amino acid sequence selected from the group consisting of:

(a) the amino acid sequence of SEQ ID NO:2;

(b) an amino acid sequence selected from the group consisting of: amino acid 542 through amino acid 579 of SEQ ID NO:2, and amino acid 464 through amino acid 583 of SEQ ID NO:2;

(c) an amino acid sequence selected from the group consisting of: amino acids 185 through 195 of SEQ ID NO:2, amino acids 213 through 223 of SEQ ID NO:2, amino acids 190 through 218 of SEQ ID NO:2, and amino acids 185 through 223 of SEQ ID NO:2;

(d) a fragment of the amino acid sequences of any of (a)-(c) comprising at least 20 contiguous amino acids;

(e) a fragment of the amino acid sequences of any of (a)-(c) comprising at least 30 contiguous amino acids;

(f) a fragment of the amino acid sequences of any of (a)-(c) having IMX97018 polypeptide activity;

(g) a fragment of the amino acid sequences of any of (a)-(c) comprising AXH domain amino acid sequences;

(h) amino acid sequences comprising at least 20 amino acids and sharing amino acid identity with the amino acid sequences of any of (a)-(g), wherein the percent amino acid identity is selected from the group consisting of: at least 75%, at least 80%, at least 85%, at least 90%, at least 95%, at least 97.5%, at least 99%, and at least 99.5%;

(i) an amino acid sequence of (h), wherein a polypeptide comprising said amino acid sequence of (h) binds to an antibody that also binds to a polypeptide comprising an amino acid sequence of any of (a)-(g); and (j) an amino acid sequence of (h) or (i) having IMX97018 polypeptide activity.

Other aspects of the invention are isolated nucleic acids encoding polypeptides of the invention, with a preferred embodiment being an isolated nucleic acid consisting of, or more preferably, comprising a nucleotide sequence selected from the group consisting of:

(a) SEQ ID NO:1; and (b) an allelic variant of (a).

The invention also provides an isolated genomic nucleic acid corresponding to the nucleic acids of the invention.

Other aspects of the invention are isolated nucleic acids encoding polypeptides of the invention, and isolated nucleic acids, preferably having a length of at least 15 nucleotides, and preferably at least 50% of the length of SEQ ID NO:1, that hybridize under conditions of moderate stringency to the nucleic acids encoding polypeptides of the invention. In preferred embodiments of the invention, such nucleic acids encode a polypeptide having IMX97018 polypeptide activity, or comprise a nucleotide sequence that shares nucleotide sequence identity with the nucleotide sequences of the nucleic acids of the invention, wherein the percent nucleotide sequence identity is selected from the group consisting of: at least 70%, at least 75%, at least 80%, at least 85%, at least 90%, at least 95%, at least 97.5%, at least 99%, and at least 99.5%.

Further provided by the invention are expression vectors and recombinant host cells comprising at least one nucleic acid of the invention, and preferred recombinant host cells wherein said nucleic acid is integrated into the host cell genome.

Also provided is a process for producing a polypeptide encoded by the nucleic acids of the invention, comprising culturing a recombinant host cell under conditions promoting expression of said polypeptide, wherein the recombinant host cell comprises at least one nucleic acid of the invention. A preferred process provided by the invention further comprises purifying said polypeptide. In another aspect of the invention, the polypeptide produced by said process is provided.

Further aspects of the invention are isolated antibodies that bind to the polypeptides of the invention, preferably monoclonal antibodies, also preferably humanized antibodies or humanized antibodies, and preferably wherein the antibody inhibits the activity of said polypeptides.

The invention additionally provides a method of designing an inhibitor of the polypeptides of the invention, the method comprising the steps of determining the three-dimensional structure of any such polypeptide, analyzing the three-dimensional structure for the likely binding sites of substrates, synthesizing a molecule that incorporates a predicted reactive site, and determining the polypeptide-inhibiting activity of the molecule. In a further aspect of the invention, a method is provided for identifying compounds that alter IMX97018 polypeptide activity comprising (a) mixing a test compound with a polypeptide of the invention; and (b) determining whether the test compound alters the IMX97018 polypeptide activity of said polypeptide.

In another aspect of the invention, a method is provided identifying compounds that inhibit the binding activity of IMX97018 polypeptides comprising (a) mixing a test compound with a polypeptide of the invention and a binding partner of said polypeptide; and (b) determining whether the test compound inhibits the binding activity of said polypeptide.

In preferred embodiments, the binding partner is a nuclear polypeptide; more preferably, the binding partner is a leucine-rich polypeptide, and still more preferably, the binding partner is a LANP polypeptide.

Further provided by the invention is a method for decreasing SCA-promoting activity of IMX97018polyQ polypeptides, comprising providing at least one antagonist of the polypeptides of the invention; with a preferred embodiment of the method further comprising decreasing said activities in a patient by administering at least one antagonist of the polypeptides of the invention, and with a further preferred embodiment wherein the antagonist is an antisense molecule that inhibits the activity of any of said polypeptides, and with a most preferred embodiment wherein the antagonist specifically inhibits the activity of polyglutamine-containing forms of said polypeptides.

An additional aspect of the invention is a method for promoting cell death comprising providing at least one compound selected from the group consisting of an IMX97018polyQ polypeptide and agonists of said polypeptides. Further provided by the invention is a method for inhibiting cell death activity comprising providing at least one antagonist of an IMX97018polyQ polypeptide, for example wherein the cell death activity is inhibited in neuronal cells.

The invention additionally provides a method for treating a oncologic condition comprising administering at least one compound selected from the group consisting of an IMX9701 polypeptide and agonists of said polypeptide. In additional aspects of the invention, the oncologic condition is selected from the group consisting of brain tumors, glioma, glioblastoma, astrocytoma, oligodendroglioma, ependymoma, ganglioglioma, medulloblastoma, neuroectodermal tumors, and pilocytic astrocytoma.

Also provided by the invention is a method for treating a neurological condition comprising administering at least one compound selected from the group consisting of an IMX97018polyQ polypeptide and agonists of said polypeptides, wherein the conditional is characterized by excess neurological activity. In addition, the invention provides a method for treating a neurological condition comprising administering an antagonist an IMX97018polyQvpolypeptide. In further aspects of the invention, the neurological condition is selected from the group consisting of dementia, including AIDS-related dementia and Alzheimer's.

In a further aspect of the invention, a method is provided for treating a neuromuscular condition comprising administering an antagonist of an IMX97018polyQ polypeptide, for example wherein the neuromuscular condition is ataxia.

In other aspects of the invention, a method is provided for treating a neurological condition comprising administering an antagonist of the polypeptide of the invention; with a preferred embodiment wherein the neurological condition is SCA4.

A further embodiment of the invention provides a use for antagonists of the polypeptides of the invention in the preparation of a medicament for treating a neurological condition; with a preferred embodiment wherein the neurological condition is SCA4.

An additional aspect of the invention provides methods for mapping and diagnosing genetic disorders linked to human chromosome 16, wherein the disorder is preferably SCA4.

DETAILED DESCRIPTION OF THE INVENTION

Similarities of IMX97018 Structure to Ataxin-1 Polypeptides

We have identified IMX97018, a new ataxin-1-like polypeptide having structural features characteristic of mammalian ataxin-1 polypeptides; the amino acid sequence of an IMX97018 polypeptide is provided in SEQ ID NO:2, and an alignment showing the sequence similarities between IMX97018 and other ataxin-I polypeptides is presented in Table 1 in Example 1 below. Collectively, the set of polypeptides comprising IMX97018 and the ataxin-1 polypeptides presented in Table 1, along with ataxin-1 homologues from other species, are referred to as 'ataxin-1-like' polypeptides. The ataxin-1-like polypeptides shown in Table 1 display a high degree of similarity to each other, with the mammalian ataxin-1 polypeptides extremely similar to each other, and IMX97018 polypeptide sharing about 39% amino acid identity with human ataxin-1 and the mammalian ataxin-1 homologues.

The typical structural elements common to ataxin-1 polypeptides include an AXH domain, an ataxin-1 self-association domain, and an RNA-binding domain, and in some forms of ataxin-1 polypeptides, a polyglutamine tract resulting from expansion of CAG triplet repeats in the coding sequence (see Table 1 below). The AXH domain has been identified as a domain of 120 amino acids (SEQ ID NO:6) common to ataxin-1 polypeptides from several species, and also some HMG-box-containing polypeptides (HMG box containing protein 1 [Homo sapiens], GenBank AAB71862; HMG-box containing protein 1 [Homo sapiens], GenBank.NP_036389; and HMG-box containing protein 1 [Rattus norvegicus], GenBank NP 037353; interestingly, HMG-box-containing polypeptides have been implicated in regulation of transcription initiation). Table 1 in Example 1 shows the location of the AXH domain within ataxin-1 and IMX97018 polypeptides, from amino acid 464 through amino acid 583 of SEQ ID NO:2, with a particularly strong match between the AXH domain and the IMX97018 polypeptide from amino acid 542 through amino acid 579 of SEQ ID NO:2. A region within the ataxin-1 polypeptide sufficient for self-association in a yeast two-hybrid assay system is present at approximately amino acids 495 through 605 of human ataxin-1 (SEQ ID NO:3) (Burright et al., 1997, *Hum Molec Genet* 6: 513-518), which corresponds to amino acids 431 through 499 of IMX97018 polypeptide (SEQ ID NO:2). This ataxin-1 self-association region is distinct from expanded polyglutamine tracts that are also implicated in self-association of ataxin-1-like polypeptides. A region of ataxin-1 polypeptide required for RNA-binding activity extends from amino acid 541 through amino acid 767 of SEQ ID NO:4 (Yue et al., 2001, *Hum Mol Genet* 10: 25-30); amino acids 444 through 640 of IMX97018 polypeptide (SEQ ID NO:2) align with this portion of ataxin-1. The portion of IMX97018 polypeptide that shows the greatest degree of similarity to the ataxin-1 self-association region are approximately amino acids 465 through 499 of SEQ ID NO:2, and the portion of IMX97018 polypeptide that shows the greatest degree of similarity to the ataxin-1 RNA-binding region are approximately amino acids 465 through 590 of SEQ ID NO:2; these portions of IMX97018 polypeptide are also those that approximately correspond to the AXH domain (amino acid 464 through amino acid 583 of SEQ ID NO:2). The human ataxin-1 polypeptide amino acid sequence shown as SEQ ID NO:3 has a polyglutamine tract of 28 Gln residues with two interspersed His residues from amino acid 197 to amino acid 226 of SEQ ID NO:3. The murine and rat ataxin-1 amino acid sequences shown as SEQ ID NO:4 and SEQ ID NO:5 have only two Gln residues at the position corresponding to the polyglutamine tract in human ataxin-1. While IMX97018 does not have a polyglutamine tract, it does have two glutamine residues encoded by CAG codons in the region corresponding to the polyglutamine tract of human ataxin-1: amino acid 190 and amino acid 218 of SEQ ID NO:2. The region of SEQ ID NO:2 corresponding to the polyglutamine tract of human ataxin-1 therefore preferably includes at least one of these Gln residues, or amino acids 185 through 195 of SEQ ID NO:2, amino acids 213 through 223 of SEQ ID NO:2, amino acids 190 through 218 of SEQ ID NO:2, or amino acids 185 through 223 of SEQ ID NO:2. IMX97018 polypeptides of the invention include isolated naturally occurring polypeptides having polyglutamine tracts, and IMX97018 polypeptides produced so as to include a polyglutamine tract; such polyglutamine-containing IMX97018 polypeptides are referred to as 'IMX97018polyQ polypeptides' herein. Preferably, such polyglutamine tracts are greater than 30 contiguous glutamine and/or histidine residues in length; such polyglutamine tracts having more than 30 residues are referred to as expanded polyglutamine tracts. More preferably, such polyglutamine tracts are 50 or more (or 60 or more, or 70 or more, or 80 or more, or 90 or more, or 100 or more, or 150 or more, or 200 or more, or 300 or more) contiguous glutamine and/or histidine residues in length. In IMX97018 polypeptides having polyglutamine tracts, the polyglutamine sequence is preferably inserted in the polyglutamine region of the IMX97018 polypeptide, i.e. at a position between amino acids 185 through 223 of SEQ ID NO:2; and more preferably between amino acids 185 through 195, amino acids 213 through 223, or amino acids 190 through 218 of SEQ ID NO:2; and most preferably at the glutamine residue at amino acid 190 or at amino acid 218 of SEQ ID NO:2.

Therefore, IMX97018 polypeptide has an overall structure consistent with other ataxin-1-like polypeptides. The skilled artisan will recognize that the boundaries of the regions of IMX97018 polypeptides described above are approximate and that the precise boundaries of such domains, as for example the boundaries of the region corresponding to the human ataxin-1 polyglutamine tract, can also differ from member to member within ataxin-1-like polypeptide family.

Biological Activities and Functions of IMX97018 Polypeptides

Typical biological activities or functions associated with ataxin-1 and ataxin-1-like polypeptides include RNA-binding activity and self-association activity. For ataxin-1 and ataxin-1-like polypeptides comprising expanded polyglutamine tracts, activities associated with such polypeptides include promoting the formation of nuclear inclusions; binding to nuclear polypeptides, for example to leucine-rich polypeptides such as LANP; down-regulating certain genes expressed in neural tissue; and promoting cell death, preferably through a non-apoptotic mechanism. The RNA-binding and self-association activities of ataxin-1 are associated with a portion of the C-terminal portion of the polypeptide which includes the AXH domain. Thus, for uses requiring RNA-binding activity, preferred IMX97018 polypeptides include those having the RNA-binding region, that is, amino acids 465 through 590 of SEQ ID NO:2 and more preferably amino acids 465 through 583 of SEQ ID NO:2. For uses requiring self-association activity, preferred IMX97018 polypeptides include those having the self-association region, that is, amino acids 465 through 499 of SEQ ID NO:2. Preferred IMX97018 polypeptides further include oligomers or fusion polypeptides comprising at least one AXH domain portion of one or more IMX97018 polypeptides, and fragments of any of these polypeptides that have RNA-binding activity or self-association activity. The RNA-binding activity of IMX97018 polypeptides can be determined, for example, in an assay that measures the amount of radiolabeled IMX97018 polypeptide that binds to agarose beads coated with a ribohomopolymer such as poly(rG). IMX97018 polypeptides (those without expanded polyglutamine tracts) having RNA-binding activity preferably have at least 25% (more preferably, at least 50%, and most preferably, at least 75%) of the RNA-binding activity of ataxin-1 having a 30-glutamine tract as measured in Yue et al., 2001, *Hum Mol Genet* 10: 25-30 (see FIG. 4). Ataxin-1-like polypeptides with expanded polyglutamine tracts (i.e. having more than 30 contiguous glutamine and/or histidine residues) are expected to have less RNA-binding activity in such assays than ataxin-1 having a 30-glutamine tract. The self-association activity of IMX97018 polypeptides can be determined, for example, in a yeast two-hybrid assay in which both the DNA-binding fusion protein and the activation-domain fusion protein contain IMX97018 polypeptides comprising the self-association region. IMX97018 polypeptides having self-association activity preferably have at least 25% (more preferably, at least 50%, and most preferably, at least 75%) of the self-association activity of ataxin-1 having a 30-glutamine tract as measured in a quantitative assay, such as the ONPG assay of Burright et al., 1997, *Hum Molec Genet* 6: 513-518 (see Table 2 on p. 514 of Burright et al.).

IMX97018 polypeptides, such as those having expanded polyglutamine tracts, which have nuclear inclusion formation activity promote the formation of IMX97018-immunoreactive nuclear aggregates. Additional activities of IMX97018 polypeptides, such as those having expanded polyglutamine tracts, include binding to leucine-rich nuclear polypeptides; down-regulation of certain genes expressed in neural tissue; and promotion of cell death. These activities are associated with the region of IMX97018 polypeptides corresponding to the polyglutamine tract of human ataxin-1 polypeptide. Thus, for uses requiring nuclear inclusion formation activity, leucine-rich nuclear polypeptide binding activity, neural gene down-regulation activity, or promotion of cell death activity, preferred IMX97018 polypeptides include those having the polyglutamine region and exhibiting one or more of the above biological activities; further preferred IMX97018 polypeptides include those having the an expanded polyglutamine tract and exhibiting one or more of the above biological activities. Preferred IMX97018 polypeptides further include oligomers or fusion polypeptides comprising at least one polyglutamine region of one or more IMX97018 polypeptides, and fragments of any of these polypeptides that have one or more of the above polyglutamine-associated activities. The nuclear inclusion formation activity and the cell death promotion activity of IMX97018 polypeptides can be determined, for example, through immunohistochemical and microscopic imaging techniques, such as confocal microscopy as used by Skinner et al. (1998, *Nature* 389: 971-974), or electron microscopy as used by Evert et al. (1999, *Hum Mol Genet* 8: 1169-1176). IMX97018 polypeptides having nuclear inclusion formation activity preferably promote nuclear inclusion formation in at least 10% (more preferably, at least 25%, and most preferably, at least 50%) of the percentage of cells having nuclear inclusions, when such cells express human ataxin-1 with a polyglutamine tract of 82 residues, when measured as in Skinner et al., 1998, *Nature* 389: 971-974. IMX97018 polypeptides having cell death promotion activity preferably promote cell death in at least 10% (more preferably, at least 25%, and most preferably, at least 50%) of the percentage of necrotic cells, when such cells express human ataxin-1 with a polyglutamine tract of 70 residues, when measured as in Evert et al., 1999, *Hum Mol Genet* 8: 1169-1176. The neural gene down-regulation activity of IMX97018 polypeptides can be determined, for example, through assays such as Northern blots of RNA from neural cells expressing IMX97018 polypeptides, or quantitative PCR from such cells, where the probe(s) or primers are specific for particular genes expressed in neural cells. IMX97018 polypeptides having neural gene down-regulation activity preferably have at least 10% (more preferably, at least 25%, and most preferably, at least 50%) of the neural gene down-regulation activity of human ataxin-1 with a polyglutamine tract of 82 residues, as measured by quantification of Northern blot band intensity.

The term "IMX97018 polypeptide activity," as used herein, includes any one or more of the following: RNA-binding activity, self-association activity, nuclear inclusion formation promoting activity, leucine-rich nuclear protein binding activity, neural gene down-regulation activity, and cell death promoting activity, as well as the ex vivo and in vivo activities of IMX97018 family polypeptides. The degree to which individual members of the IMX97018 polypeptide family and fragments and other derivatives of these polypeptides exhibit these activities can be determined by standard assay methods, particularly assays such as those referred to above. Exemplary assays are disclosed herein; those of skill in the art will appreciate that other, similar types of assays can be used to measure IMX97018 family biological activities.

An aspect of the biological activity of IMX97018 polypeptides is the ability of members of this polypeptide family to bind particular binding partners such as nuclear polypeptides, particularly leucine-rich nuclear polypeptides, and most particularly LANP polypeptides, with this binding activity associated with the region of IMX97018 polypeptide corresponding to the polyglutamine tract of ataxin-1, and in another embodiment, with the polyglutamine tract in IMX97018 polypeptides having such a polyglutamine tract. The term "binding partner," as used herein, includes ligands, receptors, substrates, antibodies, other IMX97018 polypeptides, the same IMX97018 polypeptide (in the case of homotypic interactions), and any other molecule that interacts with an IMX97018 polypeptide through contact or proximity between particular portions of the binding partner and the IMX97018 polypeptide. Because the polyglutamine region or tract of IMX97018 polypeptides binds to leucine-rich polypeptides, the polyglutamine region or tract when expressed as a separate fragment from the rest of an IMX97018 polypeptide, or as a soluble polypeptide, fused for example to an immunoglobulin Fc domain, is expected to disrupt the binding of IMX97018 polypeptides to their binding partners. By binding to one or more binding partners, the separate polyglutamine region or tract polypeptide likely prevents binding by native IMX97018 polypeptide(s), and so acts in a dominant negative fashion to inhibit the biological activities mediated via binding of IMX97018 polypeptides to binding partners such as leucine-rich nuclear polypeptides. Particularly suitable assays to detect or measure the binding between IMX97018 polypeptides and their binding partners are yeast two-hybrid assays and in vitro binding assays.

IMX97018 polypeptides are involved in neurological diseases or conditions, that share as a common feature disruption of neural cell morphology and neural cell death in their etiology. More specifically, the following neurological conditions are those that are known or are likely to involve the biological activities of IMX97018 polypeptides: spinocerebellar ataxia; particularly spinocerebellar ataxia type 4 (SCA4). Blocking or inhibiting the interactions between members of the IMX97018 polypeptide family and their substrates, ligands, receptors, binding partners, and or other interacting polypeptides is an aspect of the invention and provides methods for treating or ameliorating these diseases and conditions through the use of inhibitors of IMX97018 polypeptide activity. Examples of such inhibitors or antagonists are described in more detail below. For certain conditions involving too little IMX97018 polypeptide activity, methods of treating or ameliorating these conditions comprise increasing the amount or activity of IMX97018 polypeptides by providing isolated IMX97018 polypeptides or active fragments or fusion polypeptides thereof, or by providing compounds (agonists) that activate endogenous or exogenous IMX97018 polypeptides.

Additional uses for IMX97018 polypeptides include diagnostic reagents for diseases linked to human chromosome 16 and/or neurological disorders such as ataxic conditions, and research reagents for investigation of polyglutamine-containing polypeptides.

IMX97018 Polypeptides

An IMX97018 polypeptide is a polypeptide that shares a sufficient degree of amino acid identity or similarity to the IMX97018 polypeptide of SEQ ID NO:2 to (A) be identified by those of skill in the art as a polypeptide likely to share particular structural domains and/or (B) have biological activities in common with the UMX97018 polypeptide of SEQ ID NO:2 and/or (C) bind to antibodies that also specifically bind to other IMX97018 polypeptides. IMX97018 polypeptides can be isolated from naturally occurring sources, or have the same structure as naturally occurring IMX97018 polypeptides, or can be produced to have structures that differ from naturally occurring IMX97018 polypeptides. Polypeptides derived from any IMX97018 polypeptide by any type of alteration (for example, but not limited to, insertions, deletions, or substitutions of amino acids; changes in the state of glycosylation of the polypeptide; refolding or isomerization to change its three-dimensional structure or self-association state; and changes to its association with other polypeptides or molecules) are also IMX97018 polypeptides. Therefore, the polypeptides provided by the invention include polypeptides characterized by amino acid sequences similar to those of the IMX97018 polypeptides described herein, but into which modifications are naturally provided or deliberately engineered. A polypeptide that shares biological activities in common with IMX97018 polypeptides is a polypeptide having IMX97018 polypeptide activity. Examples of biological activities exhibited by IMX97018 polypeptides include, without limitation, RNA-binding activity, self-association activity, nuclear inclusion formation promoting activity, leucine-rich nuclear protein binding activity, neural gene down-regulation activity, and cell death promoting activity.

The present invention provides both full-length and mature forms of IMX97018 polypeptides. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides can be encoded from a single genetic locus if multiple mRNA forms are produced from that locus by alternative splicing or by the use of multiple translation initiation sites. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide can be obtained by expression, in a suitable mammalian cell or other host cell, of a nucleic acid molecule that encodes the full-length polypeptide. The sequence of the mature form of the polypeptide may also be determinable from the amino acid sequence of the full-length form, through identification of signal sequences or protease cleavage sites. The IMX97018 polypeptides of the invention also include those that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1-5 terminal amino acids).

The invention further includes IMX97018 polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as $E.\ coli$, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the invention can be incubated with a molar excess of glycopeptidase (Boehringer Mannheim).

Species homologues of IMX97018 polypeptides and of nucleic acids encoding them are also provided by the present invention. As used herein, a "species homologue" is a polypeptide or nucleic acid with a different species of origin from that of a given polypeptide or nucleic acid, but with significant sequence similarity to the given polypeptide or nucleic acid, as determined by those of skill in the art. Species homologues can be isolated and identified by making suitable probes or primers from polynucleotides encoding the amino acid sequences provided herein and screening a suitable nucleic acid source from the desired species. The invention also encompasses allelic variants of IMX97018 polypeptides and nucleic acids encoding them; that is, naturally-occurring alternative forms of such polypeptides and nucleic acids in which differences in amino acid or nucleotide sequence are attributable to genetic polymorphism (allelic variation among individuals within a population).

Fragments of the IMX97018 polypeptides of the present invention are encompassed by the present invention and can be in linear form or cydlized using known methods, for example, as described in Saragovi et al., BiotIechnology 10, 773-778 (1992) and in McDowell et at, J. Amer. Chem. Soc.

114 9245-9253 (1992). Polypeptides and polypeptide fragments of the present invention, and nucleic acids encoding them, include polypeptides and nucleic acids with amino acid or nucleotide sequence lengths that are at least 25% (more preferably at least 50%, or at least 60%, or at least 70%, and most preferably at least 80%) of the length of an 1MX97018 polypeptide and have at least 60% sequence identity (mote preferably at least 70%, at least 75%, at least 80%, at least 85%, at least 90%, at least 95%, at least 97.5%, or at least 99%, and most preferably at least 99.5%) with that 1MX97018 polypeptide or encoding nucleic acid, where sequence identity is determined by comparing the amino acid sequences of the polypeptides when aligned so as to maximize overlap and identity while minimizing sequence gaps. Also included in the present invention are polypeptides and polypeptide fragments, and nucleic acids encoding tern, that contain or encode a segment preferably comprising at least 8, or at least 10, or preferably at least 15, or more preferably at least 20, or still more preferably at least 30, or most preferably at least 40 contiguous amino acids. Such polypeptides and polyp eptide fragments may also contain a segment that shares at least 70% sequence identity (more preferably at least 70%, at least 75%, at least 8013/0, at least 85%, at least 90%, at least 95%, at least 97.5%, or at least 99%, and most preferably at least 99.5%) with any such segment of any IMX97018 polypeptide, where sequence identity is determined by comparing the amino acid sequences of the polypeptides when aligned so as to maximize overlap and identity while minimizing sequence gaps. The percent identity of two amino acid or two nucleic acid sequences can be determined by visual inspection and mathematical calculation, or more preferably, the comparison is done by comparing sequence information using a computer program. An exemplary, preferred computer program is the Genetics Computer Group ((3CC; Madison, WI) Wisconsin package version 10.0 program, 'Gap' (Devereux C at, 1984, *Nuci. Acids Res.* 12: 387). The preferred detfaultparameters for the 'GAP' program includes: (1) The GCG implementation of a unary comparison matrix (containing a value of 1 for identifies and 0 for non-identities) for nucleotides, and the weighted amino acid comparison matrix of Gribskov and Burgess, *Nuci. Acids Res.* 14:6745, 1986, as described by Schwartz and Dayhoff, edt, *Atlas of .Polypeptide Sequence and Structure*, National Biomedical Research Foundation, pp. 353-35 8, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.0.9, available for use via the National Library of Medicine website or the UW-BLAST 2.0 algorithm. In addition, the BLAST algorithm uses the BLOSUM62 amino acid scoring matrix, and optional parameters that can be used are as foflows: (A) inclusion of a filter to mask segments of the query sequence that have low compositional complexity (as determined by the SEQ program of Wootton and Federhen (Computers and Chemistry. 1993); also see Wootton and Federhen, 1996, Analysis of compositionally biased regions in sequence databases, *Methods Enrymot* 266: 554-71) or segments consisting of short-periodicity internal repeats (as determined by the XNU program of Claverie and States (Computers and Chemistry. 1993)), and (B) a statistical significance threshold for reporting matches against database sequences, or fl-score (the expected probability of matches being found merely by chance, according to the stochastic model of Karlin and Altschul (1990); if the statistical significance ascribed to a match is greater than this E-score threshold, the match will not be reported.); preferred fl-score threshold values are 0.5, or in order of increasing preference, 0.25, 0.1, 0.05, 0.01, 0.001, 0.0001, 1e-5, 1e-lO, 1e-15, 1e -20, 1e-25, 1e.-30, 1e-40, 1e-SO, 1e-75, or 1e-100.

The present invention also provides for soluble forms of IMX97018 polypeptides comprising certain fragments or domains of these polypeptides, and particularly those comprising the AXH domain, the polyglutamine region or tract, or one or more fragments of these domains. Soluble polypeptides are polypeptides that are capable of being secreted from the cells in which they are expressed. Soluble IMX97018 polypeptides include those forms of IMX97018 polypeptide that are capable of being secreted from a cell, such as those to which a signal peptide has been fused to the N-terminal end, and preferably those that retain IMX97018 polypeptide activity. Soluble IMX97018 polypeptides further include oligomers or fusion polypeptides, and fragments of any of these polypeptides that have IMX97018 polypeptide activity. A secreted soluble polypeptide can be identified (and distinguished from its non-soluble counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of IMX97018 polypeptides is advantageous for many applications. Purification of the polypeptides from recombinant host cells is facilitated, since the soluble polypeptides are secreted from the cells. Moreover, soluble polypeptides are generally more suitable for parenteral administration and for many enzymatic procedures.

In another aspect of the invention, preferred polypeptides comprise various combinations of IMX97018 polypeptide domains, such as the AXH domain and the polyglutamine region or tract. Accordingly, polypeptides of the present invention and nucleic acids encoding them include those comprising or encoding two or more copies of a domain such as the AXH domain domain, two or more copies of a domain such as the polyglutamine region or tract, or at least one copy of each domain, and these domains can be presented in any order within such polypeptides.

Further modifications in the peptide or DNA sequences can be made by those skilled in the art using known techniques. Modifications of interest in the polypeptide sequences can include the alteration, substitution, replacement, insertion or deletion of a selected amino acid. For example, one or more of the cysteine residues can be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. No. 5,071,972 and EP 276,846. Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide or a substantial equivalent thereof. One example is a variant that binds with essentially the same binding affinity as does the native form. Binding affinity can be measured by conventional procedures, e.g., as described in U.S. Pat. No. 5,512,457 and as set forth herein.

Other derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Encompassed by the invention are oligomers or fusion polypeptides that contain an IMX97018 polypeptide, one or more fragments of IMX97018 polypeptides, or any of the derivative or variant forms of IMX97018 polypeptides as disclosed herein. In particular embodiments, the oligomers comprise soluble IMX97018 polypeptides. Oligomers can be in the form of covalently linked or non-covalently-linked multimers, including dimers, trimers, or higher oligomers. In one aspect of the invention, the oligomers maintain the binding ability of the polypeptide components and provide therefor, bivalent, trivalent, etc., binding sites. In an alternative embodiment the invention is directed to oligomers comprising multiple IMX97018 polypeptides joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

In embodiments where variants of the IMX97018 polypeptides are constructed to include a membrane-spanning domain, they will form a Type I membrane polypeptide.

Immunoglobulin-based Oligomers. The polypeptides of the invention or fragments thereof can be fused to molecules such as immunoglobulins for many purposes, including increasing the valency of polypeptide binding sites. For example, fragments of an IMX97018 polypeptide can be fused directly or through linker sequences to the Fc portion of an immunoglobulin. For a bivalent form of the polypeptide, such a fusion could be to the Fc portion of an IgG molecule. Other immunoglobulin isotypes can also be used to generate such fusions. For example, a polypeptide-IgM fusion would generate a decavalent form of the polypeptide of the invention. The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred Fc polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Polypeptides", in *Current Protocols in Immunology*, Suppl. 4, pages 10.19.1-10.19.11, 1992). Methods for preparation and use of immunoglobulin-based oligomers are well known in the art. One embodiment of the present invention is directed to a dimer comprising two fusion polypeptides created by fusing a polypeptide of the invention to an Fc polypeptide derived from an antibody. A gene fusion encoding the polypeptide/Fc fusion polypeptide is inserted into an appropriate expression vector. Polypeptide/Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four IMX97018 extracellular regions.

Peptide-linker Based Oligomers. Alternatively, the oligomer is a fusion polypeptide comprising multiple IMX97018 polypeptides, with or without peptide linkers (spacer peptides). Among the suitable peptide linkers are those described in U.S. Pat. Nos. 4,751,180 and 4,935,233. A DNA sequence encoding a desired peptide linker can be inserted between, and in the same reading frame as, the DNA sequences of the invention, using any suitable conventional technique. For example, a chemically synthesized oligonucleotide encoding the linker can be ligated between the sequences. In particular embodiments, a fusion polypeptide comprises from two to four soluble IMX97018 polypeptides, separated by peptide linkers. Suitable peptide linkers, their combination with other polypeptides, and their use are well known by those skilled in the art.

Leucine-Ziplers. Another method for preparing the oligomers of the invention involves use of a leucine zipper. Leucine zipper domains are peptides that promote oligomerization of the polypeptides in which they are found. Leucine zippers were originally identified in several DNA-binding polypeptides (Landschulz et al., *Science* 240:1759, 1988), and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

Other fragments and derivatives of the sequences of polypeptides which would be expected to retain polypeptide activity in whole or in part and may thus be useful for screening or other immunological methodologies can also be made by those skilled in the art given the disclosures herein. Such modifications are believed to be encompassed by the present invention.

Nucleic Acids Encoding IMX97018 Polypeptides

Encompassed within the invention are nucleic acids encoding IMX97018 polypeptides, such as SEQ ID NO:1, which encodes the IMX97018 polypeptide of SEQ ID NO:2. These nucleic acids can be identified in several ways, including isolation of genomic or cDNA molecules from a suitable source. Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding an IMX97018 polypeptide or a desired combination of IMX97018 polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning. A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

"An isolated nucleic acid consisting essentially of a nucleotide sequence" means that the nucleic acid may have, in addition to said nucleotide sequence, additional material covalently linked to either or both ends of the nucleic acid molecule, said additional material preferably between 1 and 100,000 additional nucleotides covalently linked to either end, each end, or both ends of the nucleic acid molecule, and more preferably between 1 and 10,000 additional nucleotides covalently linked to either end, each end, or both ends of the nucleic acid molecule, and most preferably between 10 and 1,000 additional nucleotides covalently linked to either end, each end, or both ends of the nucleic acid molecule. An isolated nucleic acid consisting essentially of a nucleotide sequence may be an expression vector or other construct comprising said nucleotide sequence. "An isolated nucleic acid consisting essentially of a nucleotide sequence" further is meant to exclude isolated human chromosomes or isolated contigs such as GenBank accession number AC009127.

The present invention also includes nucleic acids that hybridize under moderately stringent conditions, and more preferably highly stringent conditions, to nucleic acids encoding IMX97018 polypeptides described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 m$^{-1}$ M EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6(log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 85%, at least 90%, at least 95%, at least 97.5%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The present invention also provides genes corresponding to the nucleic acid sequences disclosed herein. "Corresponding genes" or "corresponding genomic nucleic acids" are the regions of the genome that are transcribed to produce the mRNAs from which cDNA nucleic acid sequences are derived and can include contiguous regions of the genome necessary for the regulated expression of such genes. Corresponding genes can therefore include but are not limited to coding sequences, 5' and 3' untranslated regions, alternatively spliced exons, introns, promoters, enhancers, and silencer or suppressor elements. Corresponding genomic nucleic acids can include 10000 basepairs (more preferably, 5000 basepairs, still more preferably, 2500 basepairs, and most preferably, 1000 basepairs) of genomic nucleic acid sequence upstream of the first nucleotide of the genomic sequence corresponding to the initiation codon of the IMX97018 coding sequence, and 10000 basepairs (more preferably, 5000 basepairs, still more preferably, 2500 basepairs, and most preferably, 1000 basepairs) of genomic nucleic acid sequence downstream of the last nucleotide of the genomic sequence corresponding to the termination codon of the IMX97018 coding sequence. The corresponding genes or genomic nucleic acids can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" or "an isolated genomic nucleic acid" is a genomic nucleic acid that has been separated from the adjacent genomic sequences present in the genome of the organism from which the genomic nucleic acid was isolated.

Methods for Making and Purifying IMX97018 Polypeptides

Methods for making IMX97018 polypeptides are described below. Expression, isolation, and purification of the polypeptides and fragments of the invention can be accomplished by any suitable technique, including but not limited to the following methods. The isolated nucleic acid of the invention can be operably linked to an expression control sequence such as the pDC409 vector (Giri et al., 1990, *EMBO J.*, 13: 2821) or the derivative pDC412 vector (Wiley et al., 1995, Immunity 3: 673). The pDC400 series vectors are useful for transient mammalian expression systems, such as CV-1 or 293 cells. Alternatively, the isolated nucleic acid of the invention can be linked to expression vectors such as pDC312, pDC316, or pDC317 vectors. The pDC300 series vectors all contain the SV40 origin of replication, the CMV promoter, the adenovirus tripartite leader, and the SV40 polyA and termination signals, and are useful for stable mammalian expression systems, such as CHO cells or their derivatives. Other expression control sequences and cloning technologies can also be used to produce the polypeptide recombinantly, such as the pMT2 or pED expression vectors (Kaufman et al., 1991, Nucleic Acids Res. 19: 4485-4490; and Pouwels et al., 1985, *Cloning Vectors. A Laboratory Manual*, Elsevier, New York) and the GATEWAY Vectors (lifetech.com/Content/Tech-Online/molecular_biology/manuals_pps/11797016.pdf; Life Technologies; Rockville, Md.). In the GATEWAY system the isolated nucleic acid of the invention, flanked by attB sequences, can be recombined through an integrase reaction with a GATEWAY vector such as pDONR201 containing attP sequences. This provides an entry vector for the GATEWAY system containing the isolated nucleic acid of the invention. This entry vector can be further recombined with other suitably prepared expression control sequences, such as those of the pDC400 and pDC300 series described above. Many suitable expression control sequences are known in the art. General methods of expressing recombinant polypeptides are also described in R. Kaufman, Methods in Enzymology 185, 537-566 (1990). As used herein "operably linked" means that the nucleic acid of the invention and an expression control sequence are situated within a construct, vector, or cell in such a way that the polypeptide encoded by the nucleic acid is expressed when appropriate molecules (such as polymerases) are present. As one embodiment of the invention, at least one expression control sequence is operably linked to the nucleic acid of the invention in a recombinant host cell or progeny thereof, the nucleic acid and/or expression control sequence having been introduced into the host cell by transformation or transfection, for example, or by any other suitable method. As another embodiment of the invention, at least one expression control sequence is integrated into the genome of a recombinant host cell such that it is operably linked to a nucleic acid sequence encoding a polypeptide of the invention. In a further embodiment of the invention, at least one expression control sequence is operably linked to a nucleic acid of the invention through the action of a trans-acting factor such as a transcription factor, either in vitro or in a recombinant host cell.

In addition, a sequence encoding an appropriate signal peptide (native or heterologous) can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal peptide (secretory leader) can be fused in frame to the nucleic acid sequence of the invention so that the DNA is initially transcribed, and the mRNA translated, into a fusion polypeptide comprising the signal peptide. A signal peptide that is functional in the intended host cells is one that promotes insertion of the polypeptide into cell membranes, and most preferably, promotes extracellular secretion of the polypeptide from that host cell. The signal peptide is preferably cleaved from the polypeptide upon membrane insertion or secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable strain for DHFR selection is CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Alternatively, IMX97018 gene products can be obtained via homologous recombination, or "gene targeting," techniques. Such techniques employ the introduction of exogenous transcription control elements (such as the CMV promoter or the like) in a particular predetermined site on the genome, to induce expression of the endogenous nucleic acid sequence of interest (see, for example, U.S. Pat. No. 5,272,071). The location of integration into a host chromosome or genome can be easily determined by one of skill in the art, given the known location and sequence of the gene. In a preferred embodiment, the present invention also contemplates the introduction of exogenous transcriptional control elements in conjunction with an amplifiable gene, to produce increased amounts of the gene product, again, without the need for isolation of the gene sequence itself from the host cell.

A number of types of cells can act as suitable host cells for expression of the polypeptide. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28: 31), HeLa cells, BHK (ATCC CRL 10) cell lines, the CV1/EBNA cell line derived from the African green monkey kidney cell line CV1 (ATCC CCL 70) (McMahan et al., 1991, EMBO J. 10: 2821, 1991), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces* strains, *Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Tex. Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. A host cell that comprises an isolated nucleic acid of the invention, preferably operably linked to at least one expression control sequence, is a "recombinant host cell".

The polypeptide of the invention can be prepared by culturing transformed host cells under culture conditions suitable to express the recombinant polypeptide. The resulting expressed polypeptide can then be purified from such culture (i.e., from culture medium or cell extracts) using known purification processes, such as selective precipitation with various salts, gel filtration, and ion exchange chromatography. The purification of the polypeptide can also include an affinity column containing agents which will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography using an antibody that specifically binds one or more IMX97018 epitopes. Alternatively, the polypeptide of the invention can also be expressed in a form which will facilitate purification. For example, it can be expressed as a fusion polypeptide, that is, it may be fused with maltose binding polypeptide (MBP), glutathione-5-transferase (GST), thioredoxin (TRX), a polyHis peptide, and/or fragments thereof. Kits for expression and purification of such fusion polypeptides are commercially available from New England BioLabs (Beverly, Mass.), Pharmacia (Piscataway, N.J.) and InVitrogen, respectively. The polypeptide can also be tagged with an epitope and subsequently purified by using a specific antibody directed to such epitope. One such epitope (FLAG®) is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. The polypeptide thus purified is substantially free of other mammalian polypeptides and is defined in accordance with the present invention as an "isolated polypeptide"; such isolated polypeptides of the invention include isolated antibodies that bind to IMX97018 polypeptides, fragments, variants, binding partners etc. The polypeptide of the invention can also be expressed as a product of transgenic animals, e.g., as a component of the milk of transgenic cows, goats, pigs, or sheep which are characterized by somatic or germ cells containing a nucleotide sequence encoding the polypeptide.

It is also possible to utilize an affinity column comprising a polypeptide-binding polypeptide of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, polypeptide-binding polypeptides, such as the anti-polypeptide antibodies of the invention or other polypeptides that can interact with the polypeptide of the invention, can be bound to a solid phase support such as a column chromatography matrix or a similar substrate suitable for identifying, separating, or purifying cells that express polypeptides of the invention on their surface. Adherence of polypeptide-binding polypeptides of the invention to a solid phase contacting surface can be accomplished by any means, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the invention on their surface bind to the fixed polypeptide-binding polypeptide and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the invention first can be incubated with a biotinylated polypeptide-binding polypeptide of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The polypeptide can also be produced by known conventional chemical synthesis. Methods for constructing the polypeptides of the present invention by synthetic means are known to those skilled in the art. The synthetically-constructed polypeptide sequences, by virtue of sharing primary, secondary or tertiary structural and/or conformational characteristics with IMX97018 polypeptides can possess biological properties in common therewith, including IMX97018 polypeptide activity. Thus, they can be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Antagonists and Agonists of IMX97018 Polypeptides

Any method which neutralizes IMX97018 polypeptides or inhibits expression of the IMX97018 genes (either transcription or translation) can be used to reduce the biological activities of IMX97018 polypeptides. In particular embodiments, antagonists inhibit the binding of at least one IMX97018 polypeptide to cells, thereby inhibiting biological activities induced by the binding of those IMX97018 polypeptides to the cells. In certain other embodiments of the invention, antagonists can be designed to reduce the level of endogenous IMX97018 gene expression, e.g., using well-known antisense or ribozyme approaches to inhibit or prevent translation of IMX97018 mRNA transcripts; triple helix approaches to inhibit transcription of IMX97018 family genes; or targeted homologous recombination to inactivate or "knock out" the IMX97018 genes or their endogenous promoters or enhancer elements. Such antisense, ribozyme, and triple helix antagonists can be designed to reduce or inhibit either unimpaired, or if appropriate, mutant IMX97018 gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to an IMX97018 mRNA. The antisense oligonucleotides will bind to the complementary target gene mRNA transcripts and prevent translation. Absolute complementarity, although preferred, is not required. A sequence "complementary" to a portion of a nucleic acid, as referred to herein, means a sequence having sufficient complementarity to be able to hybridize with the nucleic acid, forming a stable duplex (or triplex, as appropriate). In the case of double-stranded antisense nucleic acids, a single strand of the duplex DNA can thus be tested, or triplex formation can be assayed. The ability to hybridize will depend on both the degree of complementarity and the length of the antisense nucleic acid. Preferred oligonucleotides are complementary to the 5' end of the message, e.g., the 5' untranslated sequence up to and including the AUG initiation codon. However, oligonucleotides complementary to the 5'- or 3'-non-translated, non-coding regions of the IMX97018 gene transcript, or to the coding regions, could be used in an antisense approach to inhibit translation of endogenous IMX97018 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides. The oligonucleotides can be DNA or RNA or chimeric mixtures or derivatives or modified versions thereof, single-stranded or double-stranded. Chimeric oligonucleotides, oligonucleosides, or mixed oligonucleotides/oligonucleosides of the invention can be of several different types. These include a first type wherein the "gap" segment of nucleotides is positioned between 5' and 3' "wing" segments of linked nucleosides and a second "open end" type wherein the "gap" segment is located at either the 3' or the 5' terminus of the oligomeric compound (see, e.g., U.S. Pat. No. 5,985,664). Oligonucleotides of the first type are also known in the art as "gapmers" or gapped oligonucleotides. Oligonucleotides of the second type are also known in the art as "hemimers" or "wingmers". The oligonucleotide can be modified at the base moiety, sugar moiety, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., 1989, Proc Natl Acad Sci U.S.A. 86: 6553-6556; Lemaitre et al., 1987, Proc Natl Acad Sci 84: 648-652; PCT Publication No. WO88/09810), or hybridization-triggered cleavage agents or intercalating agents. (See, e.g., Zon, 1988, Pharm. Res. 5: 539-549). The antisense molecules should be delivered to cells which express the IMX97018 transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface), can be administered systemically. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous IMX97018 gene transcripts and thereby prevent translation of the IMX97018 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave IMX97018 mRNA transcripts can also be used to prevent translation of IMX97018 mRNA and expression of IMX97018 polypeptides. (See, e.g., PCT International Publication WO90/11364 and U.S. Pat. No. 5,824,519). The ribozymes that can be used in the present invention include hammerhead ribozymes (Haseloff and Gerlach, 1988, Nature, 334:585-591), RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (International Patent Application No. WO 88/04300; Been and Cech, 1986, Cell, 47:207-216). As in the antisense approach, the ribozymes can be composed of modified oligonucleotides (e.g. for improved stability, targeting, etc.) and should be delivered to cells which express the IMX97018 polypeptide in vivo. A preferred method of delivery involves using a DNA construct "encoding" the ribozyme under the control of a strong constitutive pol III or pol II promoter, so that transfected cells will produce sufficient quantities of the ribozyme to destroy endogenous IMX97018 messages and inhibit translation. Because ribozymes, unlike antisense molecules, are catalytic, a lower intracellular concentration is required for efficiency.

Alternatively, endogenous IMX97018 gene expression can be reduced by targeting deoxyribonucleotide sequences complementary to the regulatory region of the target gene (i.e., the target gene promoter and/or enhancers) to form triple helical structures that prevent transcription of the target IMX97018 gene. (See generally, Helene, 1991, Anticancer Drug Des., 6(6), 569-584; Helene, et al., 1992, Ann. N.Y. Acad. Sci., 660, 27-36; and Maher, 1992, Bioassays 14(12), 807-815).

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Oligonucleotides can be synthesized by standard methods known in the art, e.g by use of an automated DNA synthesizer (such as are commercially available from Biosearch, Applied Biosystems, etc.). As examples, phosphorothioate oligonucleotides can be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448-7451). Alternatively, RNA molecules can be generated by in vitro and in vivo transcription of DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317, 230-234; Thomas and Capecchi, 1987, Cell 51, 503-512; Thompson, et al., 1989, Cell 5, 313-321). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra), or in model organisms such as Caenorhabditis elegans where the "RNA interference" ("RNAi") technique (Grishok, Tabara, and Mello, 2000, Genetic requirements for inheritance of RNAi in C. elegans, Science 287 (5462): 2494-2497), or the introduction of transgenes (Demburg et al., 2000, Transgene-mediated cosuppression in the C. elegans germ line, Genes Dev. 14 (13): 1578-1583) are used to inhibit the expression of specific target genes. However this approach can be adapted for use in humans provided the recombinant DNA constructs are directly administered or targeted to the required site in vivo using appropriate vectors such as viral vectors.

Organisms that have enhanced, reduced, or modified expression of the gene(s) corresponding to the nucleic acid sequences disclosed herein are provided. The desired change in gene expression can be achieved through the use of antisense nucleic acids or ribozymes that bind and/or cleave the mRNA transcribed from the gene (Albert and Morris, 1994, Trends Pharmacol. Sci. 15(7): 250-254; Lavarosky et al., 1997, Biochem. Mol. Med. 62(1): 11-22; and Hampel, 1998, Prog. Nucleic Acid Res. Mol. Biol. 58: 1-39). Transgenic animals that have multiple copies of the gene(s) corresponding to the nucleic acid sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1). In addition, organisms are provided in which the gene(s) corresponding to the nucleic acid sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9): 629-633; Zwaal et al., 1993, Proc. Natl. Acad. Sci. USA 90(16): 7431-7435; Clark et al., 1994, Proc. Natl. Acad. Sci. USA 91(2): 719-722), or through homologous recombination, preferably detected by positive/negative genetic selection strategies (Mansour et al., 1988, Nature 336: 348-352; U.S. Pat. Nos. 5,464,764; 5,487,992; 5,627,059; 5,631,153; 5,614,396; 5,616,491; and 5,679,523). These organisms with altered gene expression are preferably eukaryotes and more preferably are mammals. Such organisms are useful for the development of non-human models for the study of disorders involving the corresponding gene(s), and for the development of assay systems for the identification of molecules that interact with the polypeptide product(s) of the corresponding gene(s).

Also encompassed within the invention are IMX97018 polypeptide variants with partner binding sites that have been altered in conformation so that (1) the IMX97018 variant will still bind to its partner(s), but a specified small molecule will fit into the altered binding site and block that interaction, or (2) the IMX97018 variant will no longer bind to its partner(s) unless a specified small molecule is present (see for example Bishop et al., 2000, Nature 407: 395-401). Nucleic acids encoding such altered IMX97018 polypeptides can be introduced into organisms according to methods described herein, and can replace the endogenous nucleic acid sequences encoding the corresponding IMX97018 polypeptide. Such methods allow for the interaction of a particular IMX97018 polypeptide with its binding partners to be regulated by administration of a small molecule compound to an organism, either systemically or in a localized manner.

The IMX97018 polypeptides themselves can also be employed in inhibiting a biological activity of IMX97018 in in vitro or in vivo procedures. Encompassed within the invention are AXH domains of IMX97018 polypeptides that act as "dominant negative" inhibitors of native IMX97018 polypeptide function when expressed as fragments or as components of fusion polypeptides. For example, a purified polypeptide domain of the present invention can be used to inhibit binding of IMX97018 polypeptides to endogenous binding partners. Such use effectively would block IMX97018 polypeptide interactions and inhibit IMX97018 polypeptide activities. In still another aspect of the invention, an antisense inhibitor is used to inhibit activation of the endogenous IMX97018 polypeptide.

In an alternative aspect, the invention further encompasses the use of agonists of IMX97018 polypeptide activity to treat or ameliorate the symptoms of a disease for which increased IMX97018 polypeptide activity is beneficial. Such diseases include but are not limited to neurological disorders such as ataxias. In a preferred aspect, the invention entails administering compositions comprising an IMX97018 nucleic acid or an IMX97018 polypeptide to cells in vitro, to cells ex vivo, to cells in vivo, and/or to a multicellular organism such as a vertebrate or mammal. Preferred therapeutic forms of IMX97018 are soluble forms, as described above. In still another aspect of the invention, the compositions comprise administering an IMX97018-encoding nucleic acid for expression of an IMX97018 polypeptide in a host organism for treatment of disease. Particularly preferred in this regard is expression in a human patient for treatment of a dysfunction associated with aberrant (e.g., decreased) endogenous activity of an IMX97018 family polypeptide. Furthermore, the invention encompasses the administration to cells and/or organisms of compounds found to increase the endogenous activity of IMX97018 polypeptides. One example of compounds that increase IMX97018 polypeptide activity are agonistic antibodies, preferably monoclonal antibodies, that bind to IMX97018 polypeptides or binding partners, which may increase IMX97018 polypeptide activity by causing constitutive intracellular signaling (or "ligand mimicking"), or by preventing the binding of a native inhibitor of IMX97018 polypeptide activity.

Antibodies to IMX97018 Polypeptides

Antibodies that are immunoreactive with the polypeptides of the invention are provided herein. Such antibodies specifically bind to the polypeptides via the antigen-binding sites of the antibody (as opposed to non-specific binding). In the present invention, specifically binding antibodies are those that will specifically recognize and bind with IMX97018 polypeptides, homologues, and variants, but not with other molecules. In one preferred embodiment, the antibodies are specific for the polypeptides of the present invention and do not cross-react with other polypeptides. In this manner, the IMX97018 polypeptides, fragments, variants, fusion polypeptides, etc., as set forth above can be employed as "immunogens" in producing antibodies immunoreactive therewith.

More specifically, the polypeptides, fragment, variants, fusion polypeptides, etc. contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (Janeway and Travers, *Immuno Biology* 3:9 (Garland Publishing Inc., 2nd ed. 1996)). Because folded polypeptides have complex surfaces, the number of epitopes available is quite numerous; however, due to the conformation of the polypeptide and steric hindrances, the number of antibodies that actually bind to the epitopes is less than the number of available epitopes (Janeway and Travers, *Immuno Biology* 2:14 (Garland Publishing Inc., 2nd ed. 1996)). Epitopes can be identified by any of the methods known in the art. Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, *Monoclonal Antibodies, Hybridomas: A New Dimension in Biological Analyses*, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kozbor et al., 1984, *J. Immunol.* 133:3001-3005; Cole et al., 1983, *Proc. Natl. Acad. Sci. USA* 80:2026-2030); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides of the invention are also contemplated herein. Such hybridomas can be produced and identified by conventional techniques. The hybridoma producing the mAb of this invention can be cultivated in vitro or in vivo. Production of high titers of mAbs in vivo makes this the presently preferred method of production. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. For the production of antibodies, various host animals can be immunized by injection with one or more of the following: an IMX97018 polypeptide, a fragment of an IMX97018 polypeptide, a functional equivalent of an IMX97018 polypeptide, or a mutant form of an IMX97018 polypeptide. Such host animals can include but are not limited to rabbits, guinea pigs, mice, and rats. Various adjuvants can be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies can be of any immunoglobulin class including IgG, IgM, IgE, IgA, IgD and any subclass thereof.

In addition, techniques developed for the production of "chimeric antibodies" (Takeda et al., 1985, *Nature,* 314: 452-454; Morrison et al., 1984, *Proc Natl Acad Sci USA* 81: 6851-6855; Boulianne et al., 1984, *Nature* 312: 643-646; Neuberger et al., 1985, Nature 314: 268-270) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the present invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Useful techniques for humanizing antibodies are also discussed in U.S. Pat. No. 6,054,297. Procedures to generate antibodies transgenically can be found in GB 2,272,440, U.S. Pat. Nos. 5,569,825 and 5,545,806, and related patents. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.). In another preferred embodiment, fully human antibodies for use in humans are produced by screening a library of human antibody variable domains using either phage display methods (Vaughan et al., 1998, *Nat Biotechnol.* 16(6): 535-539; and U.S. Pat. No. 5,969,108), ribosome display methods (Schaffitzel et al., 1999, *J Immunol Methods* 231(1-2): 119-135), or mRNA display methods (Wilson et al., 2001, *Proc Natl Acad Sci USA* 98(7): 3750-3755).

Antigen-binding antibody fragments that recognize specific epitopes can be generated by known techniques. For example, such fragments include but are not limited to: the F(ab')2 fragments which can be produced by pepsin digestion of the antibody molecule and the Fab fragments which can be generated by reducing the disulfide bridges of the (ab')$_2$ fragments. Alternatively, Fab expression libraries can be constructed (Huse et al., 1989, Science, 246:1275-1281) to allow rapid and easy identification of monoclonal Fab fragments with the desired specificity. Techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can also be adapted to produce single chain antibodies against IMX97018 gene products. Single chain antibodies are formed by linking the heavy and light chain fragments of the Fv region via an amino acid bridge, resulting in a single chain polypeptide. Such single chain antibodies can also be useful intracellularly (i.e., as 'intrabodies), for example as described by Marasco et al. (*J. Immunol. Methods* 231:223-238, 1999) for genetic therapy in HIV infection. In addition, antibodies to the IMX97018 polypeptide can, in turn, be utilized to generate anti-idiotype antibodies that "mimic" the IMX97018 polypeptide and that may bind to the IMX97018 polypeptide's binding partners using techniques well known to those skilled in the art. (See, e.g., Greenspan & Bona, 1993, FASEB J 7(5):437-444; and Nissinoff, 1991, *J. Immunol.* 147(8):2429-2438).

Antibodies that are immunoreactive with the polypeptides of the invention include bispecific antibodies (i.e., antibodies that are immunoreactive with the polypeptides of the invention via a first antigen binding domain, and also immunoreactive with a different polypeptide via a second antigen binding domain). A variety of bispecific antibodies have been prepared, and found useful both in vitro and in vivo (see, for example, U.S. Pat. No. 5,807,706; and Cao and Suresh, 1998, Bioconjugate Chem 9: 635-644). Numerous methods of preparing bispecific antibodies are known in the art, including the use of hybrid-hybridomas such as quadromas, which are formed by fusing two differed hybridomas, and triomas, which are formed by fusing a hybridoma with a lymphocyte (Milstein and Cuello, 1983, *Nature* 305: 537-540; U.S. Pat. No. 4,474,893; and U.S. Pat. No. 6,106,833). U.S. Pat. No. 6,060,285 discloses a process for the production of bispecific antibodies in which at least the genes for the light chain and the variable portion of the heavy chain of an antibody having a first specificity are transfected into a hybridoma cell secreting an antibody having a second specificity. Chemical coupling of antibody fragments has also been used to prepare antigen-binding molecules having specificity for two different antigens (Brennan et al., 1985, *Science* 229: 81-83; Glennie et al., *J Immunol.*, 1987, 139:2367-2375; and U.S. Pat. No. 6,010,902). Bispecific antibodies can also be produced via recombinant means, for example, by using the leucine zipper moieties from the Fos and Jun proteins (which preferentially form heterodimers) as described by Kostelny et al. (*J. Immunol.* 148:1547-4553; 1992). U.S. Pat. No. 5,582,996 discloses the use of complementary interactive domains (such as leucine zipper moieties or other lock and key interactive domain structures) to facilitate heterodimer formation in the production of bispecific antibodies. Tetravalent, bispecific molecules can be prepared by fusion of DNA encoding the heavy chain of an F(ab')2 fragment of an antibody with either DNA encoding the heavy chain of a second F(ab')2 molecule (in which the CH1 domain is replaced by a CH3 domain), or with DNA encoding a single chain FV fragment of an antibody, as described in U.S. Pat. No. 5,959,083. Expression of the resultant fusion genes in mammalian cells, together with the genes for the corresponding light chains, yields tetravalent bispecific molecules having specificity for selected antigens. Bispecific antibodies can also be produced as described in U.S. Pat. No. 5,807,706. Generally, the method involves introducing a protuberance (constructed by replacing small amino acid side chains with larger side chains) at the interface of a first polypeptide and a corresponding cavity (prepared by replacing large amino acid side chains with smaller ones) in the interface of a second polypeptide. Moreover, single-chain variable fragments (sFvs) have been prepared by covalently joining two variable domains; the resulting antibody fragments can form dimers or trimers, depending on the length of a flexible linker between the two variable domains (Kortt et al., 1997, *Protein Engineering* 10:423-433).

Screening procedures by which such antibodies can be identified are well known, and can involve immunoaffinity chromatography, for example. Antibodies can be screened for agonistic (i.e., ligand-mimicking) properties. Such antibodies, upon binding to cell surface IMX97018, induce biological effects (e.g., transduction of biological signals) similar to the biological effects induced when the IMX97018 binding partner binds to cell surface IMX97018. Agonistic antibodies can be used to induce IMX97018-mediated cell stimulatory pathways or intercellular communication. Bispecific antibodies can be identified by screening with two separate assays, or with an assay wherein the bispecific antibody serves as a bridge between the first antigen and the second antigen (the latter is coupled to a detectable moiety). Bispecific antibodies that bind IMX97018 polypeptides of the invention via a first antigen binding domain will be useful in diagnostic applications. Examples of polypeptides (or other antigens) that the inventive bispecific antibodies bind via a second antigen binding domain include LANP, other leucine-rich polypeptides, and polyglutamine-containing polypeptides.

Also provided herein are conjugates comprising a detectable (e.g., diagnostic) or therapeutic agent, attached to the antibody. Examples of such agents are presented above. The conjugates find use in in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

Rational Design of Compounds that Interact with IMX97018 Polypeptides

The goal of rational drug design is to produce structural analogs of biologically active polypeptides of interest or of small molecules with which they interact, e.g., inhibitors, agonists, antagonists, etc. Any of these examples can be used to fashion drugs which are more active or stable forms of the polypeptide or which enhance or interfere with the function of a polypeptide in vivo (Hodgson J (1991) Biotechnology 9:19-21). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the molecule. Less often, useful information regarding the structure of a polypeptide may be gained by modeling based on the structure of homologous polypeptides. In both cases, relevant structural information is used to design analogous IMX97018-like molecules, to identify efficient inhibitors, or to identify small molecules that bind IMX97018 polypeptides. Useful examples of rational drug design include molecules which have improved activity or stability as shown by Braxton S and Wells J A (1992 Biochemistry 31:7796-7801) or which act as inhibitors, agonists, or antagonists of native peptides as shown by Athauda S B et al (1993 J Biochem 113:742-746). The use of IMX97018 polypeptide structural information in molecular modeling software systems to assist in inhibitor design and in studying inhibitor-IMX97018 polypeptide interaction is also encompassed by the invention. A particular method of the invention comprises analyzing the three dimensional structure of IMX97018 polypeptides for likely binding sites of substrates, synthesizing a new molecule that incorporates a predictive reactive site, and assaying the new molecule as described further herein.

It is also possible to isolate a target-specific antibody, selected by functional assay, as described further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original antigen. The anti-id could then be used to identify and isolate peptides from banks of chemically or biologically produced peptides. The isolated peptides would then act as the pharmacore.

Assays of IMX97018 Polypeptide Activities

The purified IMX97018 polypeptides of the invention (including polypeptides, polypeptides, fragments, variants, oligomers, and other forms) are useful in a variety of assays. For example, the IMX97018 molecules of the present invention can be used to identify binding partners of IMX97018 polypeptides, which can also be used to modulate intercellular communication, cell stimulation, or immune cell activity. Alternatively, they can be used to identify non-binding-partner molecules or substances that modulate intercellular communication, cell stimulatory pathways, or immune cell activity.

Assays to Identify Binding Partners. Polypeptides of the IMX97018 family and fragments thereof can be used to identify binding partners. For example, they can be tested for the ability to bind a candidate binding partner in any suitable assay, such as a conventional binding assay. To illustrate, the IMX97018 polypeptide can be labeled with a detectable reagent (e.g., a radionuclide, chromophore, enzyme that catalyzes a colorimetric or fluorometric reaction, and the like). The labeled polypeptide is contacted with cells expressing the candidate binding partner. The cells then are washed to remove unbound labeled polypeptide, and the presence of cell-bound label is determined by a suitable technique, chosen according to the nature of the label.

One example of a binding assay procedure is as follows. A recombinant expression vector containing the candidate binding partner cDNA is constructed; the candidate binding partner can be part of a fusion protein construct that includes a leader peptide and/or a transmembrane domain, so that the candidate binding partner when expressed is located on the exterior of the cell surface. CV1-EBNA-1 cells in 10 cm$^2$ dishes are transfected with this recombinant expression vector. CV-1/EBNA-1 cells (ATCC CRL 10478) constitutively express EBV nuclear antigen-1 driven from the CMV Immediate-early enhancer/promoter. CV1-EBNA-1 was derived from the African Green Monkey kidney cell line CV-1 (ATCC CCL 70), as described by McMahan et al., (*EMBO J.* 10:2821, 1991). The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion polypeptide made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization. The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc polypeptide that has bound to the cells. In all assays, non-specific binding of $^{125}$I-antibody is assayed in the absence of the Fc fusion polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, *Ann. NY Acad. Sci.* 51:660, 1949) are generated on RS/1 (BBN Software, Boston, Mass.) run on a Microvax computer. Binding can also be detected using methods that are well suited for high-throughput screening procedures, such as scintillation proximity assays (Udenfriend et al., 1985, *Proc Natl Acad Sci USA* 82: 8672-8676), homogeneous time-resolved fluorescence methods (Park et al., 1999, *Anal Biochem* 269: 94-104), fluorescence resonance energy transfer (FRET) methods (Clegg R M, 1995, *Curr Opin Biotechnol* 6: 103-110), or methods that measure any changes in surface plasmon resonance when a bound polypeptide is exposed to a potential binding partner, using for example a biosensor such as that supplied by Biacore AB (Uppsala, Sweden). Compounds that can be assayed for binding to IMX97018 polypeptides include but are not limited to small organic molecules, such as those that are commercially available—often as part of large combinatorial chemistry compound 'libraries'—from companies such as Sigma-Aldrich (St. Louis, Mo.), Arqule (Woburn, Mass.), Enzymed (Iowa City, Iowa), Maybridge Chemical Co. (Trevillett, Cornwall, UK), MDS Panlabs (Bothell, Wash.), Pharmacopeia (Princeton, N.J.), and Trega (San Diego, Calif.). Preferred small organic molecules for screening using these assays are usually less than 10K molecular weight and can possess a number of physicochemical and pharmacological properties which enhance cell penetration, resist degradation, and/or prolong their physiological half-lives (Gibbs, J., 1994, Pharmaceutical Research in Molecular Oncology, *Cell* 79(2): 193-198). Compounds including natural products, inorganic chemicals, and biologically active materials such as proteins and toxins can also be assayed using these methods for the ability to bind to IMX97018 polypeptides.

Yeast Two-Hybrid or "Interaction Trap" Assays. Where the IMX97018 polypeptide binds or potentially binds to another polypeptide (such as, for example, in a receptor-ligand interaction), the nucleic acid encoding the IMX97018 polypeptide can also be used in interaction trap assays (such as, for example, that described in Gyuris et al., *Cell* 75:791-803 (1993)) to identify nucleic acids encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate binding partner. Competitive binding assays can be performed by conventional methodology. Reagents that can be employed in competitive binding assays include radiolabeled IMX97018 and intact cells expressing IMX97018 (endogenous or recombinant) on the cell surface. For example, a radiolabeled soluble IMX97018 fragment can be used to compete with a soluble IMX97018 variant for binding to cell surface receptors. Instead of intact cells, one could substitute a soluble binding partner/Fc fusion polypeptide bound to a solid phase through the interaction of Polypeptide A or Polypeptide G (on the solid phase) with the Fc moiety. Chromatography columns that contain Polypeptide A and Polypeptide G include those available from Pharmacia Biotech, Inc., Piscataway, N.J.

Diagnostic and Other Uses of IMX97018 Polypeptides and Nucleic Acids

The nucleic acids encoding the IMX97018 polypeptides provided by the present invention can be used for numerous diagnostic or other useful purposes. The nucleic acids of the invention can be used to express recombinant polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosome 16q22.3 or to map related gene positions; to compare with endogenous DNA sequences in patients to identify potential polyglutamine-related genetic disorders, such as spinocerebellar ataxias; as probes to hybridize and thus discover novel, related DNA sequences; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Uses of IMX97018 polypeptides and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of antibodies. Any or all nucleic acids suitable for these uses are capable of being developed into reagent grade or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987

Probes and Primers. Among the uses of the disclosed IMX97018 nucleic acids, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human IMX97018 homologues.

Chromosome Mapping. The nucleic acids encoding IMX97018 polypeptides, and the disclosed fragments and combinations of these nucleic acids, can be used by those skilled in the art using well-known techniques to identify human chromosome 16, and in particular the 16q22.3 region of that chromosome, to which these nucleic acids map. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

Diagnostics and Gene Therapy. The nucleic acids encoding IMX97018 polypeptides, and the disclosed fragments and combinations of these nucleic acids can be used by one skilled in the art as a positional marker to map other genes of unknown location using well-known techniques. The nucleic acid encoding IMX97018 polypeptide has been located to a particular position on human chromosome 16q22.3 and can be used to map genetic disorders relative to that location, or to more precisely map human genetic disorders already known to be linked to chromosome 16. For example, the following genetic disorders are located near the chromosomal position of IX97018-encoding sequences, but the genes associated with these disorders have not yet been identified: Zonular Cataract (also called Perinuclear Cataract, Lamellar Cataract, Marner Cataract); Wilms Tumor Gene 3 (WT3); Acute Myelogenous Leukemia (AMLCR2), North American Indian Childhood Cirrhosis (CIRHIA, NAIC). As discussed below, another genetic disorder that maps closely to IMX97018-encoding sequences is Spinocerebellar Ataxia 4 (SCA4). IMX97018-encoding nucleic acids can be used to analyze genetic abnormalities associated with the SCA4 disorder, for example, enabling one of skill in the art to distinguish SCA4 kindreds in which chromosomal regions comprising IMX97018-encoding sequences are rearranged or deleted. There is substantial utility in nucleic acids that can be used to confirm or to eliminate SCA4 as a genetic factor for a kindred presenting with hereditary ataxia. For example, elimination of the known forms of SCA is the first step in diagnosing a family with a hereditary ataxia (see, for example, Devos et al., 2001, *Neurology* 56: 234-238). Further, assuming that the SCA4 gene overlaps with or corresponds to UMX97018-encoding sequences, the IMX97018-encoding nucleic acids can be used to identify genetic alterations in the SCA4 gene at the nucleotide level. Additionally, the IMX97018-encoding nucleic acids can be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Methods of Screening for Binding Partners. The IMX97018 polypeptides of the invention each can be used as reagents in methods to screen for or identify binding partners.

For example, the IMX97018 polypeptides can be attached to a solid support material and may bind to their binding partners in a manner similar to affinity chromatography. In particular embodiments, a polypeptide is attached to a solid support by conventional procedures. As one example, chromatography columns containing functional groups that will react with functional groups on amino acid side chains of polypeptides are available (Pharmacia Biotech, Inc., Piscataway, N.J.). In an alternative, a polypeptide/Fc polypeptide (as discussed above) is attached to protein A- or protein G-containing chromatography columns through interaction with the Fc moiety. Purified IMX97018 polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, IMX97018 polypeptides can be conjugated to a detectable moiety, then incubated with cells to be tested for binding partner expression. After incubation, unbound labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them.

Measuring Biological Activity. Polypeptides also find use in measuring the biological activity of IMX97018-binding polypeptides in terms of their binding affinity. The polypeptides thus can be employed by those conducting "quality assurance" studies, e.g., to monitor shelf life and stability of polypeptide under different conditions. For example, the polypeptides can be employed in a binding affinity study to measure the biological activity of a binding partner polypeptide that has been stored at different temperatures, or produced in different cell types. The polypeptides also can be used to determine whether biological activity is retained after modification of a binding partner polypeptide (e.g., chemical modification, truncation, mutation, etc.). The binding affinity of the modified polypeptide is compared to that of an unmodified binding polypeptide to detect any adverse impact of the modifications on biological activity of the binding polypeptide. The biological activity of a binding polypeptide thus can be ascertained before it is used in a research study, for example.

Carriers and Delivery Agents. The polypeptides also find use as carriers for delivering agents attached thereto to cells comprising identified binding partners. In one method of the invention, the IMX97018 polypeptide is covalently linked to a protein-transduction domain (PTD) such as, but not limited to, TAT, Antp, or VP22 (Schwarze et al., 2000, *Cell Biology* 10: 290-295). The polypeptides thus can be used to deliver diagnostic or therapeutic agents into such cells in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

Treating Diseases with IMX97018 Polypeptides and Antagonists Thereof

The IMX97018 polypeptides, fragments, variants, antagonists, agonists, antibodies, and binding partners of the invention are likely to be useful for treating medical conditions and diseases including, but not limited to, neurological and SCA conditions as described further herein. The therapeutic molecule or molecules to be used will depend on the etiology of the condition to be treated and the biological pathways involved, and variants, fragments, and binding partners of IMX97018 polypeptides may have effects similar to or different from IMX97018 polypeptides. For example, an antagonist of the SCA-promoting activity of IMX97018 polypeptides containing polyglutamine tracts ('IMX97018polyQ polypeptides') can be selected for treatment of conditions involving expansion of polyglutamine tracts, but a particular fragment of a given IMX97018 polypeptide itself, such as a fragment comprising the AXH domain, may also act as an effective dominant negative antagonist of that activity. Therefore, in the following paragraphs "IMX97018 polypeptides or antagonists" refers to all IMX97018 polypeptides, fragments, variants, antagonists, agonists, antibodies, and binding partners etc. of the invention, and it is understood that a specific molecule or molecules can be selected from those provided as embodiments of the invention by individuals of skill in the art, according to the biological and therapeutic considerations described herein.

Antagonists of IMX97018polyQ polypeptides and IMX97018 polypeptides and agonists are useful for treating SCA-related disorders including Spinocerebellar atrophy I (SCA1), Olivopontocerebellar atrophy I (OPCA1), Menzel type OPCA, Spinocerebellar atrophy IV (SCA4), and Spinocerebellar ataxia, autosomal dominant, with sensory axonal neuropathy; ataxia; progressive loss of muscle coordination and tone; dementia; Alzheimer's disease, disorders of vertebral disk or column development; Bell's palsy; transmissible dementia, including Creutzfeld-Jacob disease; demyelinating neuropathy; Guillain-Barre syndrome; myasthenia gravis; silent cerebral ischemia; sleep disorders, including insomnia, narcolepsy, and sleep apnea; chronic neuronal degeneration; stroke, including cerebral ischemic diseases; and neurological conditions such as those associated with the following symptoms: progressive cerebellar ataxia, cerebellar ataxia of gait and limbs, supranuclear ophthalmoplegia, pyramidal or extrapyramidal signs, mild dementia, peripheral neuropathy, macular and retinal degeneration, upper motor neuron signs, extensor plantar responses, involuntary choreiform movements, abnormal eye movements, abnormal saccade amplitude or velocity, presence of gaze-evoked nystagmus, hypermetria, lower bulbar palsies, hyperreflexia, scanning and explosive speech, incoordination, slow motor-nerve conduction, atrophy of the cerebellum, pons and olives, degeneration of lower cranial nerve nuclei, and atrophy of the dorsal columns and spinocerebellar tracts, abnormal deep tendon reflexes, reduced aspartic acid and/or markedly elevated taurine content in brain tissue, reduction in platelet glutamate dehydrogenase activity, lack of activation of GDH by ADP in either the presence or the absence of Triton, neuronal loss from the pars compacta of the substantia nigra or in the locus coeruleus, severe atrophy of the dentatorubral pathways, severe loss of Purkinje cells and degeneration of the olivocerebellar pathways, atrophy of the nucleus pontis, marked atrophy of Clarke columns and the spinocerebellar tracts, diplopia, severe spasticity or pronounced peripheral neuropathy, impaired temperature discrimination, abnormal peripheral and central motor conduction times in motor evoked potentials, pontine and cerebellar atrophy, enlargement of the fourth ventricle, gait disturbance, difficulty with fine motor tasks, dysarthria, vibratory and joint position sense loss, pinprick-sensation loss, loss of ankle-jerk reflexes, loss of knee-jerk reflexes, and complete areflexia. In addition, provided herein is the use of antagonists of IMX97018polyQ polypeptides and IMX97018 polypeptides and agonists to treat AIDS-related neurological conditions, such as AIDS dementia complex. Antagonists of IMX97018polyQ polypeptides are also useful for treating polyglutamine-related disorders including fragile X syndrome, myotonic dystrophy, Kennedy spinal and bulbar muscular atrophy, and Huntington disease.

Antagonists of IMX97018 polypeptides and IMX97018polyQ polypeptides and agonists are useful for promoting cell death, and particularly for promoting neural cell death via a non-apoptotic mechanism. Provided herein are methods for using antagonists of IMX97018 polypeptides, IMX97018polyQ polypeptides, IMX97018polyQ polypeptide agonists, compositions or combination therapies to treat various neural oncologic disorders including brain tumors, glioma, glioblastoma, astrocytoma, oligodendroglioma, ependymoma, ganglioglioma, medulloblastoma, neuroectodermal tumors, and pilocytic astrocytoma.

Administration of IMX97018 Polypeptides and Antagonists Thereof

This invention provides compounds, compositions, and methods for treating a patient, preferably a mammalian patient, and most preferably a human patient, who is suffering from a medical disorder, and in particular an IM4×97018-mediated disorder. Such IMX97018-mediated disorders include conditions caused (directly or indirectly) or exacerbated by binding between IMX97018 and a binding partner. For purposes of this disclosure, the terms "illness," "disease," "medical condition," "abnormal condition" and the like are used interchangeably with the term "medical disorder." The terms "treat", "treating", and "treatment" used herein includes curative, preventative (e.g., prophylactic) and palliative or ameliorative treatment. For such therapeutic uses, IMX97018 polypeptides and fragments, IMX97018 nucleic acids encoding the IMX97018 family polypeptides, and/or agonists or antagonists of the IMX97018 polypeptide such as antibodies can be administered to the patient in need through well-known means. Compositions of the present invention can contain a polypeptide in any form described herein, such as native polypeptides, variants, derivatives, oligomers, and biologically active fragments. In particular embodiments, the composition comprises a soluble polypeptide or an oligomer comprising soluble IMX97018 polypeptides.

Therapeutically Effective Amount. In practicing the method of treatment or use of the present invention, a therapeutically effective amount of a therapeutic agent of the present invention is administered to a patient having a condition to be treated, preferably to treat or ameliorate diseases associated with the activity of an IMX97018 family polypeptide. "Therapeutic agent" includes without limitation any of the EMX97018 polypeptides, fragments, and variants; nucleic acids encoding the IMX97018 family polypeptides, fragments, and variants; agonists or antagonists of the IMX97018 polypeptides such as antibodies; IMX97018 polypeptide binding partners; complexes formed from the IMX97018 family polypeptides, fragments, variants, and binding partners, etc. As used herein, the term "therapeutically effective amount" means the total amount of each therapeutic agent or other active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the patient is treated with said therapeutic agent in an amount and for a time sufficient to induce an improvement, and preferably a sustained improvement, in at least one indicator that reflects the severity of the disorder. An improvement is considered "sustained" if the patient exhibits the improvement on at least two occasions separated by one or more days, or more preferably, by one or more weeks. The degree of improvement is determined based on signs or symptoms, and determinations can also employ questionnaires that are administered to the patient, such as quality-of-life questionnaires. Various indicators that reflect the extent of the patient's illness can be assessed for determining whether the amount and time of the treatment is sufficient. The baseline value for the chosen indicator or indicators is established by examination of the patient prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as IMX97018 polypeptides or antagonists until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating injuries or other acute conditions. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Dosing. One skilled in the pertinent art will recognize that suitable dosages will vary, depending upon such factors as the nature and severity of the disorder to be treated, the patient's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose can be formulated in animal models to achieve a circulating plasma concentration range that includes the IC50 (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of polypeptide of the present invention with which to treat each individual patient. Initially, the attending physician will administer low doses of polypeptide of the present invention and observe, the patient's response. Larger doses of polypeptide of the present invention can be administered until the optimal therapeutic effect is obtained for the patient, and at that point the dosage is not increased further. It is contemplated that the various pharmaceutical compositions used to practice the method of the present invention should contain about 0.01 ng to about 100 mg (preferably about 0.1 ng to about 10 mg, more preferably about 0.1 microgram to about 1 mg) of polypeptide of the present invention per kg body weight. In one embodiment of the invention, IMX97018 polypeptides or antagonists are administered one time per week to treat the various medical disorders disclosed herein, in another embodiment is administered at least two times per week, and in another embodiment is administered at least three times per week. If injected, the effective amount of IMX97018 polypeptides or antagonists per adult dose ranges from 1-20 mg/m$^2$, and preferably is about 5-12 mg/m$^2$. Alternatively, a flat dose can be administered, whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described below are treated by administering a preparation acceptable for injection containing IMX97018 polypeptides or antagonists at 25 mg/dose, or alternatively, containing 50 mg per dose. The 25 mg or 50 mg dose can be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of IMX97018 polypeptides or antagonists one to three times per week over a period of at least three weeks, or a dose of 50 mg of IMX97018 polypeptides or antagonists one or two times per week for at least three weeks, though treatment for longer periods may be necessary to induce the desired degree of improvement. For incurable chronic conditions, the regimen can be continued indefinitely, with adjustments being made to dose and frequency if such are deemed necessary by the patient's physician. The foregoing doses are examples for an adult patient who is a person who is 18 years of age or older. For pediatric patients (age 4-17), a suitable regimen involves the subcutaneous injection of 0.4 mg/kg, up to a maximum dose of 25 mg of IMX97018 polypeptides or antagonists, administered by subcutaneous injection one or more times per week. If an antibody against an IMX97018 polypeptide is used as the IMX97018 polypeptide antagonist, a preferred dose range is 0.1 to 20 mg/kg, and more preferably is 1-10 mg/kg. Another preferred dose range for an anti-IMX97018 polypeptide antibody is 0.75 to 7.5 mg/kg of body weight. Humanized antibodies are preferred, that is, antibodies in which only the antigen-binding portion of the antibody molecule is derived from a non-human source. Such antibodies can be injected or administered intravenously.

Formulations. Compositions comprising an effective amount of an IMX97018 polypeptide of the present invention (from whatever source derived, including without limitation from recombinant and non-recombinant, sources), in combination with other components such as a physiologically acceptable diluent, carrier, or excipient, are provided herein. The term "Pharmaceutically acceptable" means a non-toxic material that does not interfere with the effectiveness of the biological activity of the active ingredient(s). Formulations suitable for administration include aqueous and non-aqueous sterile injection solutions which can contain anti-oxidants, buffers, bacteriostats and solutes which render the formulation isotonic with the blood of the recipient; and aqueous and non-aqueous sterile suspensions which can include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. In one preferred embodiment of the invention, sustained-release forms of IMX97018 polypeptides are used. Sustained-release forms suitable for use in the disclosed methods include, but are not limited to, IMX97018 polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

Combinations of Therapeutic Compounds. AN IMX97018 polypeptide of the present invention may be active in multimers (e.g., heterodimers or homodimers) or complexes with itself or other polypeptides. As a result, pharmaceutical compositions of the invention may comprise a polypeptide of the invention in such multimeric or complexed form. The pharmaceutical composition of the invention may be in the form of a complex of the polypeptide(s) of present invention along with polypeptide or peptide antigens. The invention further includes the administration of IMX97018 polypeptides or antagonists concurrently with one or more other drugs that are administered to the same patient in combination with the IMX97018 polypeptides or antagonists, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components can be administered in the same or in separate compositions, and by the same or different routes of administration. Examples of components that can be administered concurrently with the pharmaceutical compositions of the invention are: cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-17, IL-18, IFN, TNF0, TNF1, TNF2, G-CSF, Meg-CSF, thrombopoietin, stem cell factor, and erythropoietin, or inhibitors or antagonists of any of these factors. The pharmaceutical composition can further contain other agents which either enhance the activity of the polypeptide or compliment its activity or use in treatment. Such additional factors and/or agents may be included in the pharmaceutical composition to produce a synergistic effect with polypeptide of the invention, or to minimize side effects. Conversely, an IMX97018 polypeptide or antagonist of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. Additional examples of drugs to be administered concurrently include but are not limited to antivirals, antibiotics, analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, IMX97018 polypeptides or antagonists can be combined with a second IMX97018 polypeptide/antagonist, including an antibody against an IMX97018 polypeptide, or an IMX97018 polypeptide-derived peptide that acts as a competitive inhibitor of a native IMX97018 polypeptide.

Routes of Administration. Any efficacious route of administration can be used to therapeutically administer IMX97018 polypeptides or antagonists thereof, including those compositions comprising nucleic acids. Parenteral administration includes injection, for example, via intra-articular, intravenous, intramuscular, intralesional, intraperitoneal or subcutaneous routes by bolus injection or by continuous infusion, and also includes localized administration, e.g., at a site of disease or injury. Other suitable means of administration include sustained release from implants; aerosol inhalation and/or insufflation; eyedrops; vaginal or rectal suppositories; buccal preparations; oral preparations, including pills, syrups, lozenges, ice creams, or chewing gum; and topical preparations such as lotions, gels, sprays, ointments or other suitable techniques. Alternatively, polypeptideaceous IMX97018 polypeptides or antagonists may be administered by implanting cultured cells that express the polypeptide, for example, by implanting cells that express IMX97018 polypeptides or antagonists. Cells may also be cultured ex vivo in the presence of polypeptides of the present invention in order to modulate cell proliferation or to produce a desired effect on or activity in such cells. Treated cells can then be introduced in vivo for therapeutic purposes. The polypeptide of the instant invention may also be administered by the method of protein transduction. In this method, the IMX97018 polypeptide is covalently linked to a protein-transduction domain (PTD) such as, but not limited to, TAT, Antp, or VP22 (Schwarze et al., 2000, *Cell Biology* 10: 290-295). The PTD-linked peptides can then be transduced into cells by adding the peptides to tissue-culture media containing the cells (Schwarze et al., 1999, *Science* 285:1569; Lindgren et al., 2000, *TiPS* 21: 99; Derossi et al., 1998, *Cell Biology* 8: 84; WO 00/34308; WO 99/29721; and WO 99/10376). In another embodiment, the patient's own cells are induced to produce IMX97018 polypeptides or antagonists by transfection in vivo or ex vivo with a DNA that encodes IMX97018 polypeptides or antagonists. This DNA can be introduced into the patient's cells, for example, by injecting naked DNA or liposome-encapsulated DNA that encodes IMX97018 polypeptides or antagonists, or by other means of transfection. Nucleic acids of the invention can also be administered to patients by other known methods for introduction of nucleic acid into a cell or organism (including, without limitation, in the form of viral vectors or naked DNA). When IMX97018 polypeptides or antagonists are administered in combination with one or more other biologically active compounds, these can be administered by the same or by different routes, and can be administered simultaneously, separately or sequentially.

Oral Administration. When a therapeutically effective amount of polypeptide of the present invention is administered orally, polypeptide of the present invention will be in the form of a tablet, capsule, powder, solution or elixir. When administered in tablet form, the pharmaceutical composition of the invention can additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, petroleum, oils of animal or plant origin such as peanut oil, mineral oil, soybean oil, or sesame oil, or synthetic oils can be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

Intravenous Administration. When a therapeutically effective amount of polypeptide of the present invention is administered by intravenous, cutaneous or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention can also contain stabilizers, preservatives, buffers, antioxidants, or other additives known to those of skill in the art. The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Tissue Administration. For compositions of the present invention which are useful for neural tissue disorders, the therapeutic method includes administering the composition topically, systematically, or locally as an implant or device. When administered, the therapeutic composition for use in this invention is, of course, in a pyrogen-free, physiologically acceptable form. Further, the composition can desirably be encapsulated or injected in a viscous form for delivery to the site of tissue damage. Topical administration may be suitable for wound healing and tissue repair. Therapeutically useful agents other than a polypeptide of the invention or antagonist thereof which may also optionally be included in the composition as described above, can alternatively or additionally, be administered simultaneously or sequentially with the composition in the methods of the invention. The composition can include a matrix capable of delivering the polypeptide- or antagonist-containing composition to the site of tissue damage, providing a structure for the developing tissue and optimally capable of being resorbed into the body. Such matrices can be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions can be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure polypeptides or extracellular matrix components. Other potential matrices are nonbiodegradable and chemically defined, such as sintered hydroxapatite, bioglass, aluminates, or other ceramics Matrices can be comprised of combinations of any of the above mentioned types of material, such as polylactic acid and hydroxyapatite or collagen and tricalciumphosphate. The bioceramics can be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix. A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethyl-cellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly (vinyl alcohol). The amount of sequestering agent useful herein is 0.5-20 wt %, preferably 1-10 wt % based on total formulation weight, which represents the amount necessary to prevent desorption of the polypeptide or antagonist from the polymer matrix and to provide appropriate handling of the composition, yet not so much that the progenitor cells are prevented from infiltrating the matrix, thereby providing the polypeptide or antagonist the opportunity to assist the activity of the progenitor cells. In further compositions, polypeptides of the invention or antagonists thereof may be combined with other agents beneficial to the treatment of the wound or tissue in question. These agents include various growth factors such as epidermal growth factor (EGF), platelet derived growth factor (PDGF), transforming growth factors (TGF-alpha and TGF-beta), and insulin-like growth factor (IGF). The dosage regimen of a polypeptide-containing pharmaceutical composition to be used in tissue regeneration will be determined by the attending physician considering various factors which modify the action of the polypeptides, e.g., amount of tissue weight desired to be formed, the site of damage, the condition of the damaged tissue, the size of a wound, type of damaged tissue, the patient's age, sex, and diet, the severity of any infection, time of administration and other clinical factors. The dosage can vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue growth and/or repair, for example, X-rays, histomorphometric determinations, and tetracycline labeling.

Veterinary Uses. In addition to human patients, IMX97018 polypeptides and antagonists are useful in the treatment of disease conditions in non-human animals, such as pets (dogs, cats, birds, primates, etc.), domestic farm animals (horses cattle, sheep, pigs, birds, etc.), thoroughbred horses, or any animal that suffers from an IMX97018-mediated condition. In such instances, an appropriate dose can be determined according to the animal's body weight. For example, a dose of 0.2-1 mg/kg may be used. Alternatively, the dose is determined according to the animal's surface area, an exemplary dose ranging from 0.1-20 mg/m$^2$, or more preferably, from 5-12 mg/m$^2$. For small animals, such as dogs or cats, a suitable dose is 0.4 mg/kg. In a preferred embodiment, IMX97018 polypeptides or antagonists (preferably constructed from genes derived from the same species as the patient), is administered by injection or other suitable route one or more times per week until the animal's condition is improved, or it can be administered indefinitely.

Manufacture of Medicaments. The present invention also relates to the use of IMX97018 polypeptides, fragments, and variants; nucleic acids encoding the IMX97018 family polypeptides, fragments, and variants; agonists or antagonists of the IMX97018 polypeptides such as antibodies; IMX97018 polypeptide binding partners; complexes formed from the IMX97018 family polypeptides, fragments, variants, and binding partners, etc, in the manufacture of a medicament for the prevention or therapeutic treatment of each medical disorder disclosed herein.

EXAMPLES

The following examples are intended to illustrate particular embodiments and not to limit the scope of the invention.

Example 1

Identification of IMX97018, a New Human Ataxin-1-Like Polypeptide

A partial cDNA sequence was identified in a cDNA library prepared from human dendritic cells (described in U.S. Pat. No. 6,017,729, issued Jan. 25, 2000). That cDNA was used to identify a human chromosome 16 genomic contig (AC009127.8) that does include the entire IMX97018 coding sequence, shown as SEQ ID NO:1. The entire IMX97018 coding sequence was determined based on comparisons of human ataxin-1 polypeptide with all possible reading frames of AC009127, using the GCG program TFASTA. Nucleotides 1 through 2067 of SEQ ID NO:1 encode the IMX97018 polypeptide, the amino acid sequence of which is shown as SEQ ID NO:2. The approximate position of the single exon containing IMX97018 coding sequence in the AC009127.8 contig is shown in the table below, along with its location relative to SEQ ID NO:1; note that the coding sequence is in the inverse orientation with respect to the contig, and that the 5' and 3' untranslated regions may extend further along the contig sequence beyond those portions that correspond to SEQ ID NO:1, as indicated by the parentheses around the AC009127.8 positions in the table.

Corresponding position of IMX97018 gene exon in human contig AC009127.8 and in SEQ ID NO:1:

|  | Position in AC009127.8 | Position in SEQ ID NO: 1 |
|---|---|---|
| Exon 1 | (162604)-(160538) | 1-2067 |

The human genomic region corresponding to the AC009127.8 contig, 16q22, also includes the genetic map location for SCA4. SCA4 was mapped by Flanigan et al. (1996, *Am J Hum Genet* 59: 392-399) to a 6 centiMorgan region around the D16S397 marker on 16q22.1, and bounded on the distal end by D16S512 at 16q22.3. The AC009127.8 contig maps between D16S397 and D16S512 within 16q22.3. Therefore, the ataxin-1-like IMX97018 polypeptide is considered to be a strong candidate for the product of the SCA4 gene.

Additional variations of IMX97018 polypeptides are provided as naturally occurring genomic variants of the IMX97018 sequences disclosed herein; such variations may be incorporated into an IMX97018 polypeptide or nucleic acid individually or in any combination. As one example, the GGC codon encoding the Gly residue at position 428 of SEQ ID NO:2 is present as an AGC codon encoding a Ser residue in a naturally occurring variant of SEQ ID NO: 1, likely representing an allelic variation.

The amino acid sequence of IMX97018 (SEQ ID NO:2) was compared with the amino acid sequences of ataxin-1-like polypeptides—human ('Hs'), mouse ('Mm'), and rat ('Rn')— ataxin-1 (SEQ ID NO:3-SEQ ID NO:5, respectively)—using the GCG "pretty" multiple sequence alignment program, with amino acid similarity scoring matrix=blosum62, gap creation penalty=8, and gap extension penalty=1. An alignment of these sequences is shown in Table 1, and includes consensus residues which are identical among all four of the amino acid sequences in the alignment. The capitalized residues in the alignment are those which match the consensus residues. The numbering of amino acid residues in Table 1 corresponds to the position of those residues in the IMX97018 amino acid sequence (SEQ ID NO:2). The AXH ataxin-1 and HMG-box-containing conserved domain sequence (SEQ ID NO:6) has been optimally aligned with the Table 1 amino acid sequences, and residues within the AXH sequence that match the Table 1 consensus residues are capitalized.

Amino acid substitutions and other alterations (deletions, insertions, etc.) to IMX97018 amino acid sequences (e.g. SEQ ID NO:2) are predicted to be more likely to alter or disrupt IMX97018 polypeptide activities if they result in changes to the capitalized residues of the amino acid sequences as shown in Table 1, and particularly if those changes do not substitute an amino acid of similar structure (such as substitution of any one of the aliphatic residues— Ala, Gly, Leu, Ile, or Val—for another aliphatic residue), or a residue present in ataxin-1 polypeptides or the AXH domain at that conserved position. Conversely, if a change is made to an IMX97018 amino acid sequence resulting in a substitution of the residue at that position in the alignment from one of the other Table 1 ataxin-1 polypeptide or AXH domain sequences, it is less likely that such an alteration will affect the function of the altered IMX97018 polypeptide. For example, the consensus residue at position 504 in Table 1 is lysine, and the AXH domain has an aspartate at that position. Substitution of aspartate or the chemically similar glutamate for lysine at that position is considered less likely to alter the function of the polypeptide than substitution of tryptophan or tyrosine etc. Embodiments of the invention include IMX97018 polypeptides and fragments of IMX97018 polypeptides, comprising altered amino acid sequences. Altered IMX97018 polypeptide sequences share at least 30%, or more preferably at least 40%, or more preferably at least 50%, or more preferably at least 55%, or more preferably at least 60%, or more preferably at least 65%, or more preferably at least 70%, or more preferably at least 75%, or more preferably at least 80%, or more preferably at least 85%, or more preferably at least 90%, or more preferably at least 95%, or more preferably at least 97.5%, or more preferably at least 99%, or most preferably at least 99.5% amino acid identity with one or more of the amino acid sequences shown in Table 1. When IMX97018 polypeptide variants according to the invention, such as allelic variants or IMX97018 polypeptides having deliberately engineered modifications, are analyzed using the GeneFold algorithm (Tripos Inc., St. Louis, Mo., see tripos.com/admin/LitCtr/genefold app.pdf), the top five scoring template structures will be ataxin-1 or AXH-domain-containing polypeptides. The score for these top five hits, using any of the three types of score reported by GeneFold (sequence only, sequence plus local conformation preferences plus burial terms, or sequence plus local conformation preferences plus burial terms plus secondary structure) preferably will be at least 500, more preferably at least 750, and most preferably 999.9.

TABLE 1

Alignment of IMX97018 amino acid sequence with those of ataxin-1 polypeptides

| Protein (SEQ ID NO) | | |
|---|---|---|
| | 1 | 50 |
| IMX97018 (SEQ ID NO: 2) | MXpvhERsqE CLPPKKRdlP | vTSedmgrtt scstnhtpss daseWsrgvv |
| Hs ATX1 (SEQ ID NO: 3) | MKsnqERsnE CLPPKKReiP | aTSrsseeka ptlpsdnhrv egtaWlpg.n |
| Mm ATX1 (SEQ ID NO: 4) | MKsnqERtnE CLPPKKReiP | aTSrpseeka talpsdnhcv egvaWlps.t |
| Rn ATX1 (SEQ ID NO: 5) | MKsnqERsnE CLPPKKReiP | aTSrpseeka talpsdnhcv egvaWlps.t |
| | 51 | 98 |
| IMX97018 (SEQ ID NO: 2) | vagqsqaGaR vslgGdgaEa | itGLtvdqyG m.LyKvavpp atfSrtglP. |
| Hs ATX1 (SEQ ID NO: 3) | pggrghgGgR hgpaGtsvE. | .lGL...qqG igLhKalstg ldySPpsaPr |
| Mm ATX1 (SEQ ID NO: 4) | pgirghgGgR hgsaGtsgE. | .hGL....qG mgLIXalsag ldySPpsaPr |
| Rn ATX1 (SEQ ID NO: 5) | pgsrghgGgR hgpaGtSgE. | .hGL....qG mgLhKalsag ldySPpsaPr |
| | 99 | .147 |
| IMX97018 (SEQ ID NO: 2) | SVvnmspLPp tfnvassliq | hpGihypPIh YAqLpsTslQ FIG.SpYSlp |
| Hs ATX1 (SEQ ID NO: 3) | SVpvattLPa ayatpqp... | ...GtpvsPvq YAhLphT.fQ FIGsSqYSgt |
| Mm ATX1 (SEQ ID NO: 4) | SVptantLPt vypppqs... | ...GtpvsPvq YAhLshT.fQ FIGsSqYSgp |
| Rn ATX1 (SEQ ID NO: 5) | SVptantLPt vypppqs... | ...GtpvsPvq YAhLShT.fQ FIGsSqYSgp |
| | 148 | 190 |
| IMX97018 (SEQ ID NO: 2) | YAvppnFlPS pLlsPsaNla | TShlphfvpy AsllAeGATp PpQ~~~~~~ |
| Hs ATX1 (SEQ ID NO: 3) | YA...sFiPS qLipPtaNpv | TS........ AvasAaGATt PsQrsqleay |
| Mm ATX1 (SEQ ID NO: 4) | YA...gFiPS qLisPsgNpv | TS........ AvasAaGATt PsQrsqleay |
| Rn ATX1 (SEQ ID NO: 5) | YA...gFiPS qLisPpgNpv | TS........ AvnsAnGATt PsQrsqleay |
| | 191 | 197 |
| IMX97018 (SEQ ID NO: 2) | ~~~~~~~~~~ ~~~~~~~~~~ | ~~~~~~~~~~ ~~~~~~~~~~ ~~~apspahs |
| Hs | stllanmgsl sqtpghkaeq | qqqqqqqqqq qhqhqqqqqq qqqqqqqqqh |

TABLE 1-continued

Alignment of IMX97018 amino acid sequence with those of ataxin-1 polypeptides

Protein (SEQ ID NO)

ATX1(SEQ ID NO:3)

Mm ATX1(SEQ ID NO: 4)
stllanmgsl sqapghkve. .......... .......... ....pppqqh

Rn ATX1(SEQ ID NO: 5)
stllanmgsl sqapgbkve. .......... .......... ....pppqqh

```
               198                                         236
IMX97018       fnkApsatsP sgqlPh.... ...HsStqPl d....lapgr mPiyyqmsrl
(SEQ ID NO: 2)

Hs             lsrApglitP gs.pPpaqqn qyvHiSssPq ntgrtasppa iPvhlhphqt
ATX1(SEQ
ID NO: 3)

Mm             lsrAaglvnP gsppPptqqn qyiHiSssPq ssgratsppp iPvhlhphqt
ATX1(SEQ
ID NO: 4)

Rn             lgrAaglvnP gs.pPptqqn qyiHiSssPq ssgrats.pp iPvhlhpbqt
ATX1(SEQ
ID NO: 5)

237                              270
IMX97018       pagyTLhetP p.......ag aspvltPqEs .........Q sAleAaaang
(SEQ ID NO: 2)

Hs             miphTLtlgP psqvvmqyad sgshfvPrEa tkkaessrlQ qAiqAkevln
ATX1(SEQ
ID NO: 3)

Mm             miphTLtlgP ssqvvvqysd agghfvPrEs tkkaessrlQ qAmqAkevln
ATX1(SEQ
ID NO: 4)

Rn             miphTLtlgP ssqvvvqysd agghfvPrEs tkkaessrlQ qAmqAkevln
ATX1(SEQ
ID NO: 5)

271                                    313
IMX97018       GqrpreRnlv rreSe..aLd spnsKg.... .EgqglVpVv ecvvDgqlfS
(SEQ ID NO: 2)

Hs             GemeksRryg apsSadlgLg kaggKsvphp yEsrhvV.Vh pspsD...yS
ATX1(SEQ
ID NO: 3)

Mm             GemeksBryg assSvelsLg kassKsvphp yEsrhvV.Vh pspaD...yS
ATX1(SEQ
ID NO: 4)

Rn             GemeksRryg assSvelsLg ktssKsvphp yEsrhvV.Vh pspaD...yS
ATX1(SEQ
ID NO: 5)

314                    361
IMX97018       gsqtp..Rve VaapahrgTP dtDLEvQrvv galasqdyrv vaaqRkeePS
(SEQ ID NO: 2)

Hs             srdpsgvRas VmvlpnsnTP aaDLEvQq.. .......... .athRcasPS
ATX1(SEQ
ID NO: 3)

Mm             srdtsgvRgs VmvlpnssTP saDLEaQq.. .......... .tthReasPS
ATX1(SEQ
```

TABLE 1-continued

Alignment of IMX97018 amino acid sequence with those of ataxin-1 polypeptides

| Protein (SEQ ID NO) | | |
|---|---|---|
| ID NO: 4) | | |
| Rn ATX1 (SEQ ID NO: 5) | srdtsgvRgs VmvlpnssTP saDLEtQq.. .......... .athReaspS | |
| IMX97018 (SEQ ID NO: 2) | 362<br>pLN....Lsh htPdHqg... ......egrg SArnPaeLae ksqArgFYpq | 398 |
| Hs ATX1 (SEQ ID NO: 3) | tLNdksgLhI gkPgHrsyal sphtviqtth SAseP..Lpv glpAtaFYag | |
| Mm ATX1 (SEQ ID NO: 4) | tLNdksgLap rkPgHrsyal sphtviqtth SAseP..Lpv glpAtaFYag | |
| Rn ATX1 (SEQ ID NO: 5) | tLNdksgLbl gkPgHrsyal sphtviqtth SAseP..Lpv glpAtaFYag | |
| IMX97018 (SEQ ID NO: 2) | 399          434<br>shQePV..kh rplpkAmvvA ng...nLVpt GtdsgLIPVG S......... | |
| Hs ATX1 (SEQ ID NO: 3) | t.QpPVigyl sgqqqAityA gslpqhLVip GtqplLiPVG Stdmeasgaa | |
| Mn ATX1 (SEQ ID NO: 4) | t.QpPVigyl sgqqqAityA gglpqhtVip GnqplLiPVG Spdmdmpgaa | |
| Rn ATX1 (SEQ ID NO: 5) | a.QpPVigyl ssqqqAityA gglpqhLVip GtqplLiPVQ Spdmdtpgaa | |
| Self-ass'n | ʼʼʼʼʼʼʼʼʼʼʼʼʼʼ | |
| IMX97018 (SEQ ID NO: 2) | 435                                    451<br>eilVaSSld........... .......... .......... ..VQAratfP | |
| Hs ATX1 (SEQ ID NO: 3) | paiVtSSpqf aavphtfvtt alpksenfnp ealvtqaayp amVQAqihIP | |
| Mm ATX1 (SEQ ID NO: 4) | saiVtSSpqf aavphtfvtt alpksenfnp ealvtqasyp amVQAqihIP | |
| Rn ATX1 (SEQ ID NO: 5) | saiVtSSpqf aavphtfvtt alpksenfhp ealvtqaayp amVQAqihlP | |
| Self-ass'n | ʼ ʼʼʼʼʼʼʼʼʼʼʼʼʼʼʼʼʼʼʼʼʼʼʼʼʼʼʼʼʼʼʼʼʼʼʼʼʼʼʼʼʼʼʼʼʼʼʼʼ ʼ | |
| RNA-binding | ▬▬▬▬▬▬▬▬▬▬ | |
| IMX97018 (SEQ ID NO: 2) | 452                          500<br>dkeptppPit ss.hLPshFM KGaIIQLAtG ELKrVEDLqT qDFvrSAEvS | |
| Hs ATX1 (SEQ | vvqsvasPaa apptLPpyFM KGsIIQLAnG BLKkVEDLkT eDFiqSAEiS | |

TABLE 1-continued

Alignment of IMX97018 amino acid sequence with those of ataxin-1 polypeptides

| Protein (SEQ ID NO) | |
|---|---|
| ID NO: 3) | |
| Mm ATX1(SEQ ID NO: 4) | vvqsvasPtt asptLPpyFM KGsIIQLAnG ELKkVEDLkT eDFiqSAEiS |
| Rn ATX1(SEQ ID NO: 5) | vvqsvasPaa asptLPpyFM KGsIIQLAnG ELKkVEDLkT eDFiqSAEiS |
| AXH (SEQ ID NO: 6) | tvPhcFM KGtrlcLAnG snKkVEDLrT eDFirSAgeS |
| Self-ass'n | ⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀⁀ |
| RNA-binding | ▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄ |
| | 501                    550 |
| IMX97018 (SEQ ID NO: 2) | ggLKIdSSTV vdIqeSqwPG fvmIhFvVGE qqskVSiEVp pEhPFFVyGQ |
| Ms ATX1(SEQ ID NO: 3) | ndLKIdSSTV erIedShspG vaviqFaVGE hraqVSvEVI vEyPFFVfGQ |
| Mm ATX1(SEQ ID NO: 4) | ndLKIhSSTV erIeeShsPG vaviqFaVGE hraqVSvEVI vEyPFFVfGQ |
| Rn ATX1(SEQ ID NO: 5) | ndLKIdSSTV erIedShsPG vaviqFaVGE hraqVSvEVI vEyPFFVIGQ |
| AXH(SEQ ID NO: 6) | ndedlqmSTV krIgsSglPs vvtltFdpGv edalltvEcq vEhPFFVkGk |
| RNA-binding | ▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄ |
| | 551                    600 |
| IMX97018 (SEQ ID NO: 2) | GWSSCsPgRT tQLFsLPChr LqVGDVCISi sLqsLnsnSV sqascapPsq |
| Hs ATX1(SEQ ID NO: 3) | GWSSCcPeRT sQLFdLPCsk LsVGDVCISJ tLknLkngSV kkgqpvdPas |
| Mn ATX1(SEQ ID NO: 4) | GWSSCcPeRT sQLFdLPCsk LsVGDVCISl tLknLkngsV kkgqpvdPas |
| Rn ATX1(SEQ ID NO: 5) | GWSSCcPeRT SQLFdLPCsk LsVGDVCISl tLknLkngSV kkgqpvdPas |
| AXH (SEQ ID NO: 6) | GWSSCyPslT vQLygLPCce LqVGDVClSl thn |
| RNA-binding | ▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄ |
| | 601                    629 |
| IMX97018 (SEQ ID NO: 2) | .......... LgppReR... pErtv.lGSr elcdseGksq .......Pag |
| Hs ATX1(SBQ ID NO: 3) | vllkhskadg LagsRhRyae qEnginqGSa qmlsenGelk fpekmglPAa |

TABLE 1-continued

Alignment of IMX97018 amino acid sequence with those of ataxin-1 polypeptides

Protein
(SEQ ID NO)

| | |
|---|---|
| Mm ATX1(SEQ ID NO: 4) | vllkqvktds LagsRhRyae qEnginqGSa qvlsenGelk fpekiglPAa |
| Rn ATX1(SEQ ID NO: 5) | allkhaktds LagsRhRyae qEnginqGSa qvlsenGelk fpekiglPAa |
| RNA-binding | ■■■■■■ |
| | 630                    678 |
| IMX97018 (SEQ ID NO: 2) | egsrvvEPSq Pcsgaqa.cW pAPsfqrysm qgeEaraaLl rPSfIPQEVK |
| Hs ATX1(SEQ ID NO: 3) | pfltkiEPSk Paatrk.rrW sAPesrklek sedEppltLp kPSlIPQEVK |
| Mm ATX1(SEQ ID NO: 4) | pflskiEPSk PtatrkrrrW sAPetrklek sedEppltLp kPSlIPQEVK |
| Rn ATX1(SEQ ID NO: 5) | pfltkiEPSk Ptatrk.rrW sAPetrklek sedEppltLp kPSlIPQEVK |
| RNA-binding | ■■■■■■ |
| | 679   689 |
| IMX97018 SEQ ID NO: 2) | lsIEGRSNaQ K |
| Hs ATX1(SEQ ID NO: 3) | icIEGRSNvG K |
| Mn ATX1(SEQ ID NO: 4) | icIEGRSNvG K |
| Rn ATX1(SEQ ID NO: 5) | icIEGRSNvG K |

■■■ : polyglutamine tract

〰〰〰 : self-association region

▧▧▧ : RNA-binding region

Expression of polynucleotides encoding IMX97018 polypeptides. An array of polynucleotides, including polynucleotide probes specific for IMX97018-encoding sequences, was contacted with human RNA samples prepared from a variety of tissues and cell types. Low levels of expression of IMX97018-encoding sequences were detected in all samples tested.

Example 2

Monoclonal Antibodies that Bind Polypeptides of the Invention

This example illustrates a method for preparing monoclonal antibodies that bind IMX97018 polypeptides. Other conventional techniques may be used, such as those described in U.S. Pat. No. 4,411,993. Suitable immunogens that may be employed in generating such antibodies include, but are not limited to, purified IMX97018 polypeptide, an immunogenic fragment thereof, and cells expressing high levels of IMX97018 polypeptide or an immunogenic fragment thereof. DNA encoding an IMX97018 polypeptide can also be used as an immunogen, for example, as reviewed by Pardoll and Beckerleg in *Immunity* 3: 165, 1995.

Rodents (BALB/c mice or Lewis rats, for example) are immunized with IMX97018 polypeptide immunogen emulsified in an adjuvant (such as complete or incomplete Freund's adjuvant, alum, or another adjuvant, such as Ribi adjuvant R700 (Ribi, Hamilton, Mont.)), and injected in amounts ranging from 10-100 micrograms subcutaneously or intraperitoneally. DNA may be given intradermally (Raz et al., 1994, *Proc. Natl. Acad. Sci. USA* 91: 9519) or intamuscularly (Wang et al., 1993, *Proc. Natl. Acad. Sci. USA* 90: 4156); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision to test for IMX97018 polypeptide antibodies by dot-blot assay, ELISA (enzyme-linked immunosorbent assay), immunoprecipitation, or other suitable assays, such as FACS analysis of inhibition of binding of IMX97018 polypeptide to an IMX97018 polypeptide binding partner. Following detection of an appropriate antibody titer, positive animals are provided one last intravenous injection of IMX97018 polypeptide in saline. Three to four days later, the animals are sacrificed, and spleen cells are harvested and fused to a murine myeloma cell line, e.g., NS1 or preferably P3X63Ag8.653 (ATCC CRL-1580). These cell fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells may be screened by ELISA for reactivity against purified IMX97018 polypeptide by adaptations of the techniques disclosed in Engvall et al., (*Immunochem.* 8: 871, 1971) and in U.S. Pat. No. 4,703,004. A preferred screening technique is the antibody capture technique described in Beckmann et al., (*J. Immunol.* 144: 4212, 1990). Positive hybridoma cells can be injected intraperitoneally into syngeneic rodents to produce ascites containing high concentrations (for example, greater than 1 milligram per milliliter) of anti-IMX97018 polypeptide monoclonal antibodies. Alternatively, hybridoma cells can be grown in vitro in flasks or roller bottles by various techniques. Monoclonal antibodies can be purified by ammonium sulfate precipitation, followed by gel exclusion chromatography. Alternatively, affinity chromatography based upon binding of antibody to protein A or protein G can also be used, as can affinity chromatography based upon binding to IMX97018 polypeptide.

Example 3

Antisense Inhibition of IMX97018 Nucleic Acid Expression

In accordance with the present invention, a series of oligonucleotides are designed to target different regions of the IMX97018 mRNA molecule, using the nucleotide sequence of SEQ ID NO: 1 as the basis for the design of the oligonucleotides. The oligonucleotides are selected to be approximately 10, 12, 15, 18, or more preferably 20 nucleotide residues in length, and to have a predicted hybridization temperature that is at least 37 degrees C. Preferably, the oligonucleotides are selected so that some will hybridize toward the 5' region of the mRNA molecule, others will hybridize to the coding region, and still others will hybridize to the 3' region of the mRNA molecule. Methods such as those of Gray and Clark (U.S. Pat. Nos. 5,856,103 and 6,183,966) can be used to select oligonucleotides that form the most stable hybrid structures with target sequences, as such oligonucleotides are desirable for use as antisense inhibitors.

The oligonucleotides may be oligodeoxynucleotides, with phosphorothioate backbones (internucleoside linkages) throughout, or may have a variety of different types of internucleoside linkages. Generally, methods for the preparation, purification, and use of a variety of chemically modified oligonucleotides are described in U.S. Pat. No. 5,948,680. As specific examples, the following types of nucleoside phosphoramidites may be used in oligonucleotide synthesis: deoxy and 2'-alkoxy amidites; 2'-fluoro amidites such as 2'-fluorodeoxyadenosine amidites, 2'-fluorodeoxyguanosine, 2'-fluorouridine, and 2'-fluorodeoxycytidine; 2'-O-(2-methoxyethyl)-modified amidites such as 2,2'-anhydro[1-(beta-D-arabino-furanosyl)-5-methyluridine], 2'-O-methoxyethyl-5-methyluridine, 2'-O-methoxyethyl-5'-O-dimethoxytrityl-5-methyluridine, 3'-O-acetyl-2'-O-methoxy-ethyl-5'-O-dimethoxytrityl-5-methyluridine, 3'-O-acetyl-2'-O-methoxyethyl-5'-O-dimethoxytrityl-5-methyl-4-triazoleuridine, 2'-O-methoxyethyl-5'-O-dimethoxytrityl-5-methylcytidine, N4-benzoyl-2'-O-methoxyethyl-5'-O-dimethoxytrityl-5-methylcytidine, and N4-benzoyl-2'-O-methoxyethyl-5'-O-di-methoxytrityl-5-methylcytidine-3'-amidite; 2'-O-(aminooxyethyl) nucleoside amidites and 2'-O-(dimethylaminooxyethyl) nucleoside amidites such as 2'-(dimethylaminooxyethoxy) nucleoside amidites, 5'-O-tert-butyldiphenylsilyl-$O^2$-2'-anhydro-5-methyluridine, 5'-O-tert-butyl-diphenylsilyl-2'-O-(2-hydroxyethyl)-5-methyluridine, 2'-O-([2-phthalimidoxy)ethyl]-5'-t-butyldiphenyl-silyl-5-methyluridine, 5'-O-tert-butyldiphenylsilyl-2'-O-[(2-formadoximinooxy)ethyl]-5-methyluridine, 5'-O-tert-butyldiphenylsilyl-2'-O-[N,N-dimethylaminooxyethyl]-5-methyluridine, 2'-O-(dimethylaminooxy-ethyl)-5-methyluridine, 5'-O-DMT-2'-O-(dimethylaminooxyethyl)-5-methyluridine, and 5'-O-DMT-2'-O-(2-N,N-dimethylaminooxyethyl)-5-methyluridine-3'-[(2-cyanoethyl)-N,N-diisopropylphosphor-amidite]; and 2'-(aminooxyethoxy) nucleoside amidites such as N2-isobutyryl-6-O-diphenyl-carbamoyl-2'-O-(2-ethylacetyl)-5'-O-(4,4'-dimethoxytrityl) guanosine-3'-[(2-cyanoethyl)-N,N-diiso-propylphosphoramidite].

Modified oligonucleosides may also be used in oligonucleotide synthesis, for example methylenemethylimino-linked oligonucleosides, also called MMI-linked oligonucleosides; methylene-dimethylhydrazo-linked oligonucleosides, also called MDH-linked oligonucleosides; methylene-carbonylamino-linked oligonucleosides, also called amide-3-linked oligonucleosides; and methylene-aminocarbonyl-linked oligonucleosides, also called amide-4-linked oligonucleosides, as well as mixed backbone compounds having, for instance, alternating MMI and P=O or P=S linkages, which are prepared as described in U.S. Pat. Nos. 5,378,825, 5,386,023, 5,489,677, 5,602,240 and 5,610,289. Formacetal- and thioformacetal-linked oligonucleosides may also be used and are prepared as described in U.S. Pat. Nos. 5,264,562 and 5,264,564; and ethylene oxide linked oligonucleosides may also be used and are prepared as described in U.S. Pat. No. 5,223,618. Peptide nucleic acids (PNAs) may be used as in the same manner as the oligonucleotides described above, and are prepared in accordance with any of the various procedures referred to in Peptide Nucleic Acids (PNA): Synthesis, Properties and Potential Applications, Bioorganic & Medicinal Chemistry, 1996, 4, 5-23; and U.S. Pat. Nos. 5,539,082, 5,700,922, and 5,719,262.

Chimeric oligonucleotides, oligonucleosides, or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Some examples of different types of chimeric oligonucleotides are: [2'-O-Me]-[2'-deoxy]-[2'-O-Me] chimeric phosphorothioate oligonucleotides, [2'-O-(2-methoxyethyl)]-[2'-deoxy]-[2'-O-(methoxyethyl)] chimeric phosphorothioate oligonucleotides, and [2'-O-(2-methoxy-ethyl) phosphodiester]-[2'deoxy phosphoro-thioate]-[2'-O-(2-methoxyethyl)phosphodiester] chimeric oligonucleotides, all of which may be prepared according to U.S. Pat. No. 5,948,680. In one preferred embodiment, chimeric oligonucleotides ("gapmers") 18 nucleotides in length are utilized, composed of a central "gap" region consisting of ten 2'-deoxynucleotides, which is flanked on both sides (5' and 3' directions) by four-nucleotide "wings". The wings are composed of 2'-methoxyethyl (2'-MOE) nucleotides. The internucleoside (backbone) linkages are phosphorothioate (P=S) throughout the oligonucleotide. Cytidine residues in the 2'-MOE wings are 5-methylcytidines. Other chimeric oligonucleotides, chimeric oligonucleosides, and mixed chimeric oligonucleotides/oligonucleosides are synthesized according to U.S. Pat. No. 5,623,065.

Oligonucleotides are preferably synthesized via solid phase P(III) phosphoramidite chemistry on an automated synthesizer capable of assembling 96 sequences simultaneously in a standard 96 well format. The concentration of oligonucleotide in each well is assessed by dilution of samples and UV absorption spectroscopy. The full-length integrity of the individual products is evaluated by capillary electrophoresis, and base and backbone composition is confirmed by mass analysis of the compounds utilizing electrospray-mass spectroscopy.

The effect of antisense compounds on target nucleic acid expression can be tested in any of a variety of cell types provided that the target nucleic acid is present at measurable levels. This can be routinely determined using, for example, PCR or Northern blot analysis. Cells are routinely maintained for up to 10 passages as recommended by the supplier. When cells reached 80% to 90% confluency, they are treated with oligonucleotide. For cells grown in 96-well plates, wells are washed once with 200 microliters OPTI-MEM-1 reduced-serum medium (Gibco BRL) and then treated with 130 microliters of OPTI-MEM-1 containing 3.75 g/mL LIPOFECTIN (Gibco BRL) and the desired oligonucleotide at a final concentration of 150 nM. After 4 hours of treatment, the medium is replaced with fresh medium. Cells are harvested 16 hours after oligonucleotide treatment. Preferably, the effect of several different oligonucleotides should be tested simultaneously, where the oligonucleotides hybridize to different portions of the target nucleic acid molecules, in order to identify the oligonucleotides producing the greatest degree of inhibition of expression of the target nucleic acid.

Antisense modulation of IMX97018 nucleic acid expression can be assayed in a variety of ways known in the art. For example, IMX97018 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation and Northern blot analysis are taught in, for example, Ausubel, F. M. et al., Current Protocols in Molecular Biology, Volume 1, pp. 4.1.1-4.2.9 and 4.5.1-4.5.3, John Wiley & Sons, Inc., 1996. Real-time quantitative (PCR) can be conveniently accomplished using the commercially available ABI PRISM 7700 Sequence Detection System, available from PE-Applied Biosystems, Foster City, Calif. and used according to manufacturer's instructions. This fluorescence detection system allows high-throughput quantitation of PCR products. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples. Other methods of quantitative PCR analysis are also known in the art. IMX97018 protein levels can be quantitated in a variety of ways well known in the art, such as immunoprecipitation, Western blot analysis (immunoblotting), ELISA, or fluorescence-activated cell sorting (FACS). Antibodies directed to IMX97018 polypeptides can be prepared via conventional antibody generation methods such as those described herein. Immunoprecipitation methods, Western blot (immunoblot) analysis, and enzyme-linked immunosorbent assays (ELISA) are standard in the art (see, for example, Ausubel, F. M. et al., Current Protocols in Molecular Biology, Volume 2, pp. 10.16.1-10.16.11, 10.8.1-10.8.21, and 11.2.1-11.2.22, John Wiley & Sons, Inc., 1991).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| Sequences Presented in the Sequence Listing | | |
|---|---|---|
| SEQ ID NO | Type | Description |
| SEQ ID NO: 1 | Nucleotide | IMX97018 coding sequence |
| SEQ ID NO: 2 | Amino acid | IMX97018 amino acid sequence |
| SEQ ID NO: 3 | Amino acid | *Homo sapiens* ataxin-1 polypeptide (SWISSPROT accession # P54253) |

-continued

| Sequences Presented in the Sequence Listing | | |
|---|---|---|
| SEQ ID NO | Type | Description |
| SEQ ID NO: 4 | Amino acid | *Mus musculus* ataxin-1 polypeptide (SWISSPROT accession # P54254) |
| SEQ ID NO: 5 | Amino acid | *Rattus norvegicus* ataxin-1 polypeptide (GenBank accession # NP_036858) |
| SEQ ID NO: 6 | Amino acid | AXH domain (ncbi.nlm.nih.gov/Structure/cdd/cdd.shtml; smart00536) |

What is claimed is:

1. An isolated monoclonal antibody or monoclonal antibody fragment that binds to a polypeptide consisting of the amino acid sequence selected from the group consisting of (a) the amino acid sequence selected from the group consisting of: the amino acids 542 through 579 of SEQ ID NO:2, and the amino acids 464 through 583 of SEQ ID NO:2; (b) the amino acid sequence selected from the group consisting of: the amino acids 465 through 499 of SEQ ID NO:2, and the amino acids 431 through 499 of SEQ ID NO:2; and (c) the amino acid sequence selected from the group consisting of: the amino acids 465 through 590 of SEQ ID NO:2, and the amino acids 444 through 640 of SEQ ID NO:2.

2. The antibody of claim 1, wherein the antibody is a humanized or human antibody.

3. A hybridoma which produces the antibody of claim 1.

* * * * *

SEQUENCE LISTING

```
<160> NUMBER OF SEQ ID NOS: 6

<210> SEQ ID NO 1
<211> LENGTH: 2067
<212> TYPE: DNA
<213> ORGANISM: Homo sapiens

<400> SEQUENCE: 1
atgaaacctg ttcatgaaag gagtcaggaa tgccttccac caaagaaacg agacctcccc      60
gtgaccagcg aggatatggg gagaactacc agctgctcca ctaaccacac accctccagt     120
gatgcttctg aatggtcccg aggggttgtg gtggctgggc agagccaggc aggagccaga     180
gtcagcctgg ggggtgatgg agctgaggcc atcaccggtc tgacagtgga ccagtatggc     240
atgctgtata aggtggctgt gccgcctgcc accttttcac caactggact cccatctgtg     300
gtgaatatga gtcccttgcc cccaacgttt aatgtagcgt cttcactaat tcaacatcca     360
ggcatccact atcctccact ccactatgct cagctcccat ccacctcgct gcagttcatt     420
gggtctcctt atagccttcc ctatgctgtg ccacctaatt tcctaccgag tccctcctca     480
tctccttctg ccaaccttgc cacctctcac cttccacact tgtgccata tgcctcactt     540 ctggctgaag gagccactcc tcccccacag gctccctccc cggcccactc atttaacaaa     600
gctccctctg ccacctcccc atctgggcaa ttgccacatc attcaagtac tcagccgctg     660
gaccttgctc caggtcggat gcccatttat tatcagatgt ccaggctacc tgctgggtat     720
actttgcatg aaacccctcc agcaggtgcc agcccagttc ttaccccctca ggagagccag     780 tctgctctgg aagcagctgc tgcaaatgga ggacagagac cacgagagcg aaatttagta     840
agacgggaaa gtgaagccct tgactccccc aacagcaagg gtgaaggcca gggactggtg     900
ccagtggtag aatgtgtggt ggatggacag ttgttttcag gttctcagac tccacggta     960 gaggtagcag caccagcaca ccgggggacc ccggacactg accttgaggt ccagcgggtg    1020
gttggcgctt tagcttctca ggactatcgt gtggtggcag ctcagaggaa ggaggaaccc    1080 agcccctca acctatccca tcataccccc gaccatcagg tgaggggcg agggtcagcc    1140 aggaaccctg cagagctggc agagaaaagt caggcccgtg ggttctaccc tcagtcccat    1200
caggaaccag taaaacatag acctttaccc aaagcaatgg ttgtagccaa tgcaacctg     1260 gtgcccactg gaactgactc aggcctgctg cctgtgggct cggagatcct ggtagcatca    1320
agtctggacg tgcaggccag agccaccttc ccagacaagg agccaacgcc gccccccatt    1380
acctcctctc acttgccttc ccatttcatg aaaggcgcca tcatccagct ggctacggga    1440
gagctgaagc gggtggagga cctccagacc caggattttg tgcgcagtgc cgaagtgagc    1500
```

-continued

```
ggggggctga agattgactc tagcacggtc gtggacattc aggagagcca atggcctgga    1560
tttgtcatgc tgcattttgt ggttggtgag cagcagagca aagtgagcat cgaagtgccc    1620
cccgagcacc ccttctttgt atatggccag ggttggtcct cttgcagccc tgggcggacg    1680
acacaactct tctctctgcc ctgccatcgg ctacaggtgg agatgtctg catctctatc     1740 agtttacaga gcttgaacag taactcagtt tctcaggcca gctgtgctcc cccaagccag    1800
ctgggtcccc cccgagaaag gcctgagagg acggtcttgg gatccagaga gctatgtgac    1860
agtgagggga agagccagcc ggcaggagag ggctcccgtg tggtagagcc ttcccagcct    1920
gagtccggtg ctcaggcctg ctggccagcc ccgagcttcc aaagatacag catgcaaggg    1980
gaggaggcac gggctgcgct gctccgtccc tctttcattc cacaggaggt aaagctgtcc    2040
attgaagggc gttccaatgc gggaaaa                                         2067
```

<210> SEQ ID NO 2
<211> LENGTH: 689
<212> TYPE: PRT
<213> ORGANISM: Homo sapiens

<400> SEQUENCE: 2

```
Met Lys Pro Val His Glu Arg Ser Gln Glu Cys Leu Pro Pro Lys Lys
1               5                   10                  15

Arg Asp Leu Pro Val Thr Ser Glu Asp Met Gly Arg Thr Thr Ser Cys
            20                  25                  30

Ser Thr Asn His Thr Pro Ser Ser Asp Ala Ser Glu Trp Ser Arg Gly
        35                  40                  45

Val Val Val Ala Gly Gln Ser Gln Ala Gly Ala Arg Val Ser Leu Gly
    50                  55                  60

Gly Asp Gly Ala Glu Ala Ile Thr Gly Leu Thr Val Asp Gln Tyr Gly
65                  70                  75                  80

Met Leu Tyr Lys Val Ala Val Pro Pro Ala Thr Phe Ser Pro Thr Gly
                85                  90                  95

Leu Pro Ser Val Val Asn Met Ser Pro Leu Pro Pro Thr Phe Asn Val
            100                 105                 110

Ala Ser Ser Leu Ile Gln His Pro Gly Ile His Tyr Pro Pro Leu His
        115                 120                 125

Tyr Ala Gln Leu Pro Ser Thr Ser Leu Gln Phe Ile Gly Ser Pro Tyr
    130                 135                 140

Ser Leu Pro Tyr Ala Val Pro Pro Asn Phe Leu Pro Ser Pro Leu Leu
145                 150                 155                 160

Ser Pro Ser Ala Asn Leu Ala Thr Ser His Leu Pro His Phe Val Pro
                165                 170                 175

Tyr Ala Ser Leu Leu Ala Glu Gly Ala Thr Pro Pro Gln Ala Pro
            180                 185                 190

Ser Pro Ala His Ser Phe Asn Lys Ala Pro Ser Ala Thr Ser Pro Ser
        195                 200                 205

Gly Gln Leu Pro His His Ser Thr Gln Pro Leu Asp Leu Ala Pro
    210                 215                 220

Gly Arg Met Pro Ile Tyr Tyr Gln Met Ser Arg Leu Pro Ala Gly Tyr
225                 230                 235                 240

Thr Leu His Glu Thr Pro Pro Ala Gly Ala Ser Pro Val Leu Thr Pro
                245                 250                 255

Gln Glu Ser Gln Ser Ala Leu Glu Ala Ala Ala Asn Gly Gly Gln
            260                 265                 270
```

-continued

```
Arg Pro Arg Glu Arg Asn Leu Val Arg Arg Glu Ser Glu Ala Leu Asp
        275                 280                 285

Ser Pro Asn Ser Lys Gly Glu Gly Gln Gly Leu Val Pro Val Val Glu
    290                 295                 300

Cys Val Val Asp Gly Gln Leu Phe Ser Gly Ser Gln Thr Pro Arg Val
305                 310                 315                 320

Glu Val Ala Ala Pro Ala His Arg Gly Thr Pro Asp Thr Asp Leu Glu
                325                 330                 335

Val Gln Arg Val Val Gly Ala Leu Ala Ser Gln Asp Tyr Arg Val Val
            340                 345                 350

Ala Ala Gln Arg Lys Glu Glu Pro Ser Pro Leu Asn Leu Ser His His
        355                 360                 365

Thr Pro Asp His Gln Gly Glu Gly Arg Gly Ser Ala Arg Asn Pro Ala
    370                 375                 380

Glu Leu Ala Glu Lys Ser Gln Ala Arg Gly Phe Tyr Pro Gln Ser His
385                 390                 395                 400

Gln Glu Pro Val Lys His Arg Pro Leu Pro Lys Ala Met Val Val Ala
                405                 410                 415

Asn Gly Asn Leu Val Pro Thr Gly Thr Asp Ser Gly Leu Leu Pro Val
            420                 425                 430

Gly Ser Glu Ile Leu Val Ala Ser Ser Leu Asp Val Gln Ala Arg Ala
        435                 440                 445

Thr Phe Pro Asp Lys Glu Pro Thr Pro Pro Ile Thr Ser Ser His
    450                 455                 460

Leu Pro Ser His Phe Met Lys Gly Ala Ile Ile Gln Leu Ala Thr Gly
465                 470                 475                 480

Glu Leu Lys Arg Val Glu Asp Leu Gln Thr Gln Asp Phe Val Arg Ser
                485                 490                 495

Ala Glu Val Ser Gly Gly Leu Lys Ile Asp Ser Ser Thr Val Val Asp
            500                 505                 510

Ile Gln Glu Ser Gln Trp Pro Gly Phe Val Met Leu His Phe Val Val
        515                 520                 525

Gly Glu Gln Gln Ser Lys Val Ser Ile Glu Val Pro Pro Glu His Pro
    530                 535                 540

Phe Phe Val Tyr Gly Gln Gly Trp Ser Ser Cys Ser Pro Gly Arg Thr
545                 550                 555                 560

Thr Gln Leu Phe Ser Leu Pro Cys His Arg Leu Gln Val Gly Asp Val
                565                 570                 575

Cys Ile Ser Ile Ser Leu Gln Ser Leu Asn Ser Asn Ser Val Ser Gln
            580                 585                 590

Ala Ser Cys Ala Pro Pro Ser Gln Leu Gly Pro Pro Arg Glu Arg Pro
        595                 600                 605

Glu Arg Thr Val Leu Gly Ser Arg Glu Leu Cys Asp Ser Glu Gly Lys
    610                 615                 620

Ser Gln Pro Ala Gly Glu Gly Ser Arg Val Val Glu Pro Ser Gln Pro
625                 630                 635                 640

Glu Ser Gly Ala Gln Ala Cys Trp Pro Ala Pro Ser Phe Gln Arg Tyr
                645                 650                 655

Ser Met Gln Gly Glu Glu Ala Arg Ala Leu Leu Arg Pro Ser Phe
            660                 665                 670

Ile Pro Gln Glu Val Lys Leu Ser Ile Glu Gly Arg Ser Asn Ala Gly
        675                 680                 685
```

-continued

Lys

<210> SEQ ID NO 3
<211> LENGTH: 816
<212> TYPE: PRT
<213> ORGANISM: Homo sapiens

<400> SEQUENCE: 3

Met Lys Ser Asn Gln Glu Arg Ser Asn Glu Cys Leu Pro Pro Lys Lys
1               5                   10                  15

Arg Glu Ile Pro Ala Thr Ser Arg Ser Ser Glu Glu Lys Ala Pro Thr
            20                  25                  30

Leu Pro Ser Asp Asn His Arg Val Glu Gly Thr Ala Trp Leu Pro Gly
        35                  40                  45

Asn Pro Gly Gly Arg Gly His Gly Gly Arg His Gly Pro Ala Gly
    50                  55                  60

Thr Ser Val Glu Leu Gly Leu Gln Gln Gly Ile Gly Leu His Lys Ala
65              70                  75                  80

Leu Ser Thr Gly Leu Asp Tyr Ser Pro Pro Ser Ala Pro Arg Ser Val
                85                  90                  95

Pro Val Ala Thr Thr Leu Pro Ala Ala Tyr Ala Thr Pro Gln Pro Gly
            100                 105                 110

Thr Pro Val Ser Pro Val Gln Tyr Ala His Leu Pro His Thr Phe Gln
        115                 120                 125

Phe Ile Gly Ser Ser Gln Tyr Ser Gly Thr Tyr Ala Ser Phe Ile Pro
    130                 135                 140

Ser Gln Leu Ile Pro Pro Thr Ala Asn Pro Val Thr Ser Ala Val Ala
145                 150                 155                 160

Ser Ala Ala Gly Ala Thr Thr Pro Ser Gln Arg Ser Gln Leu Glu Ala
                165                 170                 175

Tyr Ser Thr Leu Leu Ala Asn Met Gly Ser Leu Ser Gln Thr Pro Gly
            180                 185                 190

His Lys Ala Glu Gln Gln Gln Gln Gln Gln Gln Gln Gln Gln Gln Gln
        195                 200                 205

His Gln His Gln Gln Gln Gln Gln Gln Gln Gln Gln Gln Gln Gln Gln
    210                 215                 220

Gln Gln His Leu Ser Arg Ala Pro Gly Leu Ile Thr Pro Gly Ser Pro
225                 230                 235                 240

Pro Pro Ala Gln Gln Asn Gln Tyr Val His Ile Ser Ser Ser Pro Gln
                245                 250                 255

Asn Thr Gly Arg Thr Ala Ser Pro Pro Ala Ile Pro Val His Leu His
            260                 265                 270

Pro His Gln Thr Met Ile Pro His Thr Leu Thr Leu Gly Pro Pro Ser
        275                 280                 285

Gln Val Val Met Gln Tyr Ala Asp Ser Gly Ser His Phe Val Pro Arg
    290                 295                 300

Glu Ala Thr Lys Lys Ala Glu Ser Ser Arg Leu Gln Gln Ala Ile Gln
305                 310                 315                 320

Ala Lys Glu Val Leu Asn Gly Glu Met Glu Lys Ser Arg Arg Tyr Gly
                325                 330                 335

Ala Pro Ser Ser Ala Asp Leu Gly Leu Gly Lys Ala Gly Gly Lys Ser
            340                 345                 350

Val Pro His Pro Tyr Glu Ser Arg His Val Val Val His Pro Ser Pro
        355                 360                 365

-continued

```
Ser Asp Tyr Ser Ser Arg Asp Pro Ser Gly Val Arg Ala Ser Val Met
    370                 375                 380
Val Leu Pro Asn Ser Asn Thr Pro Ala Ala Asp Leu Glu Val Gln Gln
385                 390                 395                 400
Ala Thr His Arg Glu Ala Ser Pro Ser Thr Leu Asn Asp Lys Ser Gly
                405                 410                 415
Leu His Leu Gly Lys Pro Gly His Arg Ser Tyr Ala Leu Ser Pro His
            420                 425                 430
Thr Val Ile Gln Thr Thr His Ser Ala Ser Glu Pro Leu Pro Val Gly
                435                 440                 445
Leu Pro Ala Thr Ala Phe Tyr Ala Gly Thr Gln Pro Pro Val Ile Gly
    450                 455                 460
Tyr Leu Ser Gly Gln Gln Gln Ala Ile Thr Tyr Ala Gly Ser Leu Pro
465                 470                 475                 480
Gln His Leu Val Ile Pro Gly Thr Gln Pro Leu Leu Ile Pro Val Gly
                485                 490                 495
Ser Thr Asp Met Glu Ala Ser Gly Ala Ala Pro Ala Ile Val Thr Ser
            500                 505                 510
Ser Pro Gln Phe Ala Ala Val Pro His Thr Phe Val Thr Thr Ala Leu
    515                 520                 525
Pro Lys Ser Glu Asn Phe Asn Pro Glu Ala Leu Val Thr Gln Ala Ala
    530                 535                 540
Tyr Pro Ala Met Val Gln Ala Gln Ile His Leu Pro Val Val Gln Ser
545                 550                 555                 560
Val Ala Ser Pro Ala Ala Ala Pro Pro Thr Leu Pro Pro Tyr Phe Met
                565                 570                 575
Lys Gly Ser Ile Ile Gln Leu Ala Asn Gly Glu Leu Lys Lys Val Glu
            580                 585                 590
Asp Leu Lys Thr Glu Asp Phe Ile Gln Ser Ala Glu Ile Ser Asn Asp
    595                 600                 605
Leu Lys Ile Asp Ser Ser Thr Val Glu Arg Ile Glu Asp Ser His Ser
    610                 615                 620
Pro Gly Val Ala Val Ile Gln Phe Ala Val Gly Glu His Arg Ala Gln
625                 630                 635                 640
Val Ser Val Glu Val Leu Val Glu Tyr Pro Phe Phe Val Phe Gly Gln
                645                 650                 655
Gly Trp Ser Ser Cys Cys Pro Glu Arg Thr Ser Gln Leu Phe Asp Leu
            660                 665                 670
Pro Cys Ser Lys Leu Ser Val Gly Asp Val Cys Ile Ser Leu Thr Leu
    675                 680                 685
Lys Asn Leu Lys Asn Gly Ser Val Lys Lys Gly Gln Pro Val Asp Pro
    690                 695                 700
Ala Ser Val Leu Leu Lys His Ser Lys Ala Asp Gly Leu Ala Gly Ser
705                 710                 715                 720
Arg His Arg Tyr Ala Glu Gln Glu Asn Gly Ile Asn Gln Gly Ser Ala
                725                 730                 735
Gln Met Leu Ser Glu Asn Gly Glu Leu Lys Phe Pro Glu Lys Met Gly
            740                 745                 750
Leu Pro Ala Ala Pro Phe Leu Thr Lys Ile Glu Pro Ser Lys Pro Ala
    755                 760                 765
Ala Thr Arg Lys Arg Arg Trp Ser Ala Pro Glu Ser Arg Lys Leu Glu
    770                 775                 780
Lys Ser Glu Asp Glu Pro Pro Leu Thr Leu Pro Lys Pro Ser Leu Ile
```

```
                785                 790                 795                 800
Pro Gln Glu Val Lys Ile Cys Ile Glu Gly Arg Ser Asn Val Gly Lys
                805                 810                 815

<210> SEQ ID NO 4
<211> LENGTH: 792
<212> TYPE: PRT
<213> ORGANISM: Mus musculus

<400> SEQUENCE: 4

Met Lys Ser Asn Gln Glu Arg Thr Asn Glu Cys Leu Pro Pro Lys Lys
1               5                   10                  15

Arg Glu Ile Pro Ala Thr Ser Arg Pro Ser Glu Glu Lys Ala Thr Ala
                20                  25                  30

Leu Pro Ser Asp Asn His Cys Val Glu Gly Val Ala Trp Leu Pro Ser
            35                  40                  45

Thr Pro Gly Ile Arg Gly His Gly Gly Arg His Gly Ser Ala Gly
        50                  55                  60

Thr Ser Gly Glu His Gly Leu Gln Gly Met Gly Leu Leu Lys Ala Leu
65              70                  75                  80

Ser Ala Gly Leu Asp Tyr Ser Pro Ser Ala Pro Arg Ser Val Pro
                85                  90                  95

Thr Ala Asn Thr Leu Pro Thr Val Tyr Pro Pro Gln Ser Gly Thr
            100                 105                 110

Pro Val Ser Pro Val Gln Tyr Ala His Leu Ser His Thr Phe Gln Phe
        115                 120                 125

Ile Gly Ser Ser Gln Tyr Ser Gly Pro Tyr Ala Gly Phe Ile Pro Ser
    130                 135                 140

Gln Leu Ile Ser Pro Ser Gly Asn Pro Val Thr Ser Ala Val Ala Ser
145                 150                 155                 160

Ala Ala Gly Ala Thr Thr Pro Ser Gln Arg Ser Gln Leu Glu Ala Tyr
                165                 170                 175

Ser Thr Leu Leu Ala Asn Met Gly Ser Leu Ser Gln Ala Pro Gly His
            180                 185                 190

Lys Val Glu Pro Pro Gln Gln His Leu Ser Arg Ala Ala Gly Leu
        195                 200                 205

Val Asn Pro Gly Ser Pro Pro Pro Thr Gln Gln Asn Gln Tyr Ile
    210                 215                 220

His Ile Ser Ser Ser Pro Gln Ser Ser Gly Arg Ala Thr Ser Pro Pro
225                 230                 235                 240

Pro Ile Pro Val His Leu His Pro His Gln Thr Met Ile Pro His Thr
                245                 250                 255

Leu Thr Leu Gly Pro Ser Ser Gln Val Val Gln Tyr Ser Asp Ala
            260                 265                 270

Gly Gly His Phe Val Pro Arg Glu Ser Thr Lys Lys Ala Glu Ser Ser
        275                 280                 285

Arg Leu Gln Gln Ala Met Gln Ala Lys Glu Val Leu Asn Gly Glu Met
    290                 295                 300

Glu Lys Ser Arg Arg Tyr Gly Ala Ser Ser Val Glu Leu Ser Leu
305                 310                 315                 320

Gly Lys Ala Ser Ser Lys Ser Val Pro His Pro Tyr Glu Ser Arg His
                325                 330                 335

Val Val Val His Pro Ser Pro Ala Asp Tyr Ser Ser Arg Asp Thr Ser
            340                 345                 350
```

-continued

```
Gly Val Arg Gly Ser Val Met Val Leu Pro Asn Ser Ser Thr Pro Ser
            355                 360                 365

Ala Asp Leu Glu Ala Gln Gln Thr Thr His Arg Glu Ala Ser Pro Ser
        370                 375                 380

Thr Leu Asn Asp Lys Ser Gly Leu Ala Pro Arg Lys Pro Gly His Arg
385                 390                 395                 400

Ser Tyr Ala Leu Ser Pro His Thr Val Ile Gln Thr Thr His Ser Ala
                405                 410                 415

Ser Glu Pro Leu Pro Val Gly Leu Pro Ala Thr Ala Phe Tyr Ala Gly
            420                 425                 430

Thr Gln Pro Pro Val Ile Gly Tyr Leu Ser Gly Gln Gln Gln Ala Ile
        435                 440                 445

Thr Tyr Ala Gly Gly Leu Pro Gln His Leu Val Ile Pro Gly Asn Gln
    450                 455                 460

Pro Leu Leu Ile Pro Val Gly Ser Pro Asp Met Asp Met Pro Gly Ala
465                 470                 475                 480

Ala Ser Ala Ile Val Thr Ser Ser Pro Gln Phe Ala Ala Val Pro His
                485                 490                 495

Thr Phe Val Thr Thr Ala Leu Pro Lys Ser Glu Asn Phe Asn Pro Glu
            500                 505                 510

Ala Leu Val Thr Gln Ala Ser Tyr Pro Ala Met Val Gln Ala Gln Ile
        515                 520                 525

His Leu Pro Val Val Gln Ser Val Ala Ser Pro Thr Thr Ala Ser Pro
    530                 535                 540

Thr Leu Pro Pro Tyr Phe Met Lys Gly Ser Ile Ile Gln Leu Ala Asn
545                 550                 555                 560

Gly Glu Leu Lys Lys Val Glu Asp Leu Lys Thr Glu Asp Phe Ile Gln
                565                 570                 575

Ser Ala Glu Ile Ser Asn Asp Leu Lys Ile His Ser Ser Thr Val Glu
            580                 585                 590

Arg Ile Glu Glu Ser His Ser Pro Gly Val Ala Val Ile Gln Phe Ala
        595                 600                 605

Val Gly Glu His Arg Ala Gln Val Ser Val Glu Val Leu Val Glu Tyr
    610                 615                 620

Pro Phe Phe Val Phe Gly Gln Gly Trp Ser Ser Cys Cys Pro Glu Arg
625                 630                 635                 640

Thr Ser Gln Leu Phe Asp Leu Pro Cys Ser Lys Leu Ser Val Gly Asp
                645                 650                 655

Val Cys Ile Ser Leu Thr Leu Lys Asn Leu Lys Asn Gly Ser Val Lys
            660                 665                 670

Lys Gly Gln Pro Val Asp Pro Ala Ser Val Leu Leu Lys Gln Val Lys
        675                 680                 685

Thr Asp Ser Leu Ala Gly Ser Arg His Arg Tyr Ala Glu Gln Glu Asn
    690                 695                 700

Gly Ile Asn Gln Gly Ser Ala Gln Val Leu Ser Glu Asn Gly Glu Leu
705                 710                 715                 720

Lys Phe Pro Glu Lys Ile Gly Leu Pro Ala Ala Pro Phe Leu Ser Lys
                725                 730                 735

Ile Glu Pro Ser Lys Pro Thr Ala Thr Arg Lys Arg Arg Arg Trp Ser
            740                 745                 750

Ala Pro Glu Thr Arg Lys Leu Glu Lys Ser Glu Asp Glu Pro Pro Leu
        755                 760                 765

Thr Leu Pro Lys Pro Ser Leu Ile Pro Gln Glu Val Lys Ile Cys Ile
```

```
                    770              775              780
Glu Gly Arg Ser Asn Val Gly Lys
785                 790

<210> SEQ ID NO 5
<211> LENGTH: 789
<212> TYPE: PRT
<213> ORGANISM: Rattus norvegicus

<400> SEQUENCE: 5

Met Lys Ser Asn Gln Glu Arg Ser Asn Glu Cys Leu Pro Pro Lys Lys
1               5                   10                  15

Arg Glu Ile Pro Ala Thr Ser Arg Pro Ser Glu Glu Lys Ala Thr Ala
            20                  25                  30

Leu Pro Ser Asp Asn His Cys Val Glu Gly Val Ala Trp Leu Pro Ser
        35                  40                  45

Thr Pro Gly Ser Arg Gly His Gly Gly Arg His Gly Pro Ala Gly
    50                  55                  60

Thr Ser Gly Glu His Gly Leu Gln Gly Met Gly Leu His Lys Ala Leu
65              70                  75                  80

Ser Ala Gly Leu Asp Tyr Ser Pro Ser Ala Pro Arg Ser Val Pro
                85                  90                  95

Thr Ala Asn Thr Leu Pro Thr Val Tyr Pro Pro Gln Ser Gly Thr
            100                 105                 110

Pro Val Ser Pro Val Gln Tyr Ala His Leu Ser His Thr Phe Gln Phe
            115                 120                 125

Ile Gly Ser Ser Gln Tyr Ser Gly Pro Tyr Ala Gly Phe Ile Pro Ser
            130                 135                 140

Gln Leu Ile Ser Pro Pro Gly Asn Pro Val Thr Ser Ala Val Ala Ser
145                 150                 155                 160

Ala Ala Gly Ala Thr Thr Pro Ser Gln Arg Ser Gln Leu Glu Ala Tyr
                165                 170                 175

Ser Thr Leu Leu Ala Asn Met Gly Ser Leu Ser Gln Ala Pro Gly His
            180                 185                 190

Lys Val Glu Pro Pro Gln Gln His Leu Gly Arg Ala Ala Gly Leu
            195                 200                 205

Val Asn Pro Gly Ser Pro Pro Thr Gln Gln Asn Gln Tyr Ile His
210                 215                 220

Ile Ser Ser Ser Pro Gln Ser Ser Gly Arg Ala Thr Ser Pro Pro Ile
225                 230                 235                 240

Pro Val His Leu His Pro His Gln Thr Met Ile Pro His Thr Leu Thr
                245                 250                 255

Leu Gly Pro Ser Ser Gln Val Val Gln Tyr Ser Asp Ala Gly Gly
            260                 265                 270

His Phe Val Pro Arg Glu Ser Thr Lys Lys Ala Glu Ser Ser Arg Leu
            275                 280                 285

Gln Gln Ala Met Gln Ala Lys Glu Val Leu Asn Gly Glu Met Glu Lys
290                 295                 300

Ser Arg Arg Tyr Gly Ala Ser Ser Val Glu Leu Ser Leu Gly Lys
305                 310                 315                 320

Thr Ser Ser Lys Ser Val Pro His Pro Tyr Glu Ser Arg His Val Val
                325                 330                 335

Val His Pro Ser Pro Ala Asp Tyr Ser Ser Arg Asp Thr Ser Gly Val
            340                 345                 350
```

-continued

```
Arg Gly Ser Val Met Val Leu Pro Asn Ser Ser Thr Pro Ser Ala Asp
        355                 360                 365
Leu Glu Thr Gln Gln Ala Thr His Arg Glu Ala Ser Pro Ser Thr Leu
        370                 375                 380
Asn Asp Lys Ser Gly Leu His Leu Gly Lys Pro Gly His Arg Ser Tyr
385                 390                 395                 400
Ala Leu Ser Pro His Thr Val Ile Gln Thr Thr His Ser Ala Ser Glu
                405                 410                 415
Pro Leu Pro Val Gly Leu Pro Ala Thr Ala Phe Tyr Ala Gly Ala Gln
                420                 425                 430
Pro Pro Val Ile Gly Tyr Leu Ser Gln Gln Gln Ala Ile Thr Tyr
        435                 440                 445
Ala Gly Gly Leu Pro Gln His Leu Val Ile Pro Gly Thr Gln Pro Leu
        450                 455                 460
Leu Ile Pro Val Gly Ser Pro Asp Met Asp Thr Pro Gly Ala Ala Ser
465                 470                 475                 480
Ala Ile Val Thr Ser Ser Pro Gln Phe Ala Ala Val Pro His Thr Phe
                485                 490                 495
Val Thr Thr Ala Leu Pro Lys Ser Glu Asn Phe Asn Pro Glu Ala Leu
                500                 505                 510
Val Thr Gln Ala Ala Tyr Pro Ala Met Val Gln Ala Gln Ile His Leu
        515                 520                 525
Pro Val Val Gln Ser Val Ala Ser Pro Ala Ala Ala Ser Pro Thr Leu
        530                 535                 540
Pro Pro Tyr Phe Met Lys Gly Ser Ile Ile Gln Leu Ala Asn Gly Glu
545                 550                 555                 560
Leu Lys Lys Val Glu Asp Leu Lys Thr Glu Asp Phe Ile Gln Ser Ala
                565                 570                 575
Glu Ile Ser Asn Asp Leu Lys Ile Asp Ser Ser Thr Val Glu Arg Ile
                580                 585                 590
Glu Asp Ser His Ser Pro Gly Val Ala Val Ile Gln Phe Ala Val Gly
        595                 600                 605
Glu His Arg Ala Gln Val Ser Val Glu Val Leu Val Glu Tyr Pro Phe
        610                 615                 620
Phe Val Phe Gly Gln Gly Trp Ser Ser Cys Cys Pro Glu Arg Thr Ser
625                 630                 635                 640
Gln Leu Phe Asp Leu Pro Cys Ser Lys Leu Ser Val Gly Asp Val Cys
                645                 650                 655
Ile Ser Leu Thr Leu Lys Asn Leu Lys Asn Gly Ser Val Lys Lys Gly
                660                 665                 670
Gln Pro Val Asp Pro Ala Ser Ala Leu Leu Lys His Ala Lys Thr Asp
        675                 680                 685
Ser Leu Ala Gly Ser Arg His Arg Tyr Ala Glu Gln Glu Asn Gly Ile
        690                 695                 700
Asn Gln Gly Ser Ala Gln Val Leu Ser Glu Asn Gly Glu Leu Lys Phe
705                 710                 715                 720
Pro Glu Lys Ile Gly Leu Pro Ala Ala Pro Phe Leu Thr Lys Ile Glu
                725                 730                 735
Pro Ser Lys Pro Thr Ala Thr Arg Lys Arg Arg Trp Ser Ala Pro Glu
                740                 745                 750
Thr Arg Lys Leu Glu Lys Ser Glu Asp Glu Pro Pro Leu Thr Leu Pro
        755                 760                 765
Lys Pro Ser Leu Ile Pro Gln Glu Val Lys Ile Cys Ile Glu Gly Arg
```

-continued

```
                  770             775             780
Ser Asn Val Gly Lys
785

<210> SEQ ID NO 6
<211> LENGTH: 120
<212> TYPE: PRT
<213> ORGANISM: Artificial Sequence
<220> FEATURE:
<223> OTHER INFORMATION: AXH domain consensus sequence

<400> SEQUENCE: 6

Thr Val Pro His Cys Phe Met Lys Gly Thr Arg Leu Cys Leu Ala Asn
1               5                   10                  15

Gly Ser Asn Lys Lys Val Glu Asp Leu Arg Thr Glu Asp Phe Ile Arg
            20                  25                  30

Ser Ala Gly Cys Ser Asn Asp Glu Asp Leu Gln Met Ser Thr Val Lys
        35                  40                  45

Arg Ile Gly Ser Ser Gly Leu Pro Ser Val Val Thr Leu Thr Phe Asp
    50                  55                  60

Pro Gly Val Glu Asp Ala Leu Leu Thr Val Glu Cys Gln Val Glu His
65                  70                  75                  80

Pro Phe Val Lys Gly Lys Gly Trp Ser Ser Cys Tyr Pro Ser Leu
                85                  90                  95

Thr Val Gln Leu Tyr Gly Leu Pro Cys Cys Glu Leu Gln Val Gly Asp
            100                 105                 110

Val Cys Leu Ser Leu Thr His Asn
            115                 120
```